US008512734B2

(12) United States Patent
Martens et al.

(10) Patent No.: US 8,512,734 B2
(45) Date of Patent: Aug. 20, 2013

(54) BIOCOMPATIBLE COATING OF MEDICAL DEVICES

(75) Inventors: Johan Martens, Huldenberg (BE); Jan Van Humbeeck, Oud-Heverlee (BE); Ivan De Scheerder, Herent (BE)

(73) Assignee: Katholieke Universiteit Leuven, K.U.Leuven R&D, Leuven (BE)

( * ) Notice: Subject to any disclaimer, the term of this patent is extended or adjusted under 35 U.S.C. 154(b) by 589 days.

(21) Appl. No.: 11/571,723

(22) PCT Filed: Jul. 5, 2005

(86) PCT No.: PCT/BE2005/000108
§ 371 (c)(1), (2), (4) Date: Jan. 5, 2007

(87) PCT Pub. No.: WO2006/002498
PCT Pub. Date: Jan. 12, 2006

(65) Prior Publication Data
US 2008/0003256 A1 Jan. 3, 2008

(30) Foreign Application Priority Data

Jul. 5, 2004 (GB) .................................. 0414911.8
Nov. 17, 2004 (GB) .................................. 0425322.5

(51) Int. Cl.
*A61F 2/00* (2006.01)
*A61K 9/00* (2006.01)

(52) U.S. Cl.
USPC .......................................... 424/425; 424/400

(58) Field of Classification Search
None
See application file for complete search history.

(56) References Cited

U.S. PATENT DOCUMENTS

| 3,948,254 | A | * | 4/1976 | Zaffaroni | 128/833 |
| 4,251,427 | A | | 2/1981 | Recker et al. | |
| 4,577,642 | A | | 3/1986 | Stokes | |
| 4,577,647 | A | * | 3/1986 | Fenster et al. | 132/219 |
| 5,902,283 | A | * | 5/1999 | Darouiche et al. | 604/265 |
| 6,274,207 | B1 | | 8/2001 | Balkus et al. | |
| 6,436,422 | B1 | * | 8/2002 | Trogolo et al. | 424/405 |
| 6,790,814 | B1 | * | 9/2004 | Marin et al. | 510/101 |
| 7,294,409 | B2 | | 11/2007 | Lye et al. | |
| 2001/0013166 | A1 | * | 8/2001 | Yan | 29/527.2 |
| 2001/0033951 | A1 | | 10/2001 | Balkus et al. | |
| 2002/0007209 | A1 | * | 1/2002 | Scheerder et al. | 623/1.15 |
| 2004/0199247 | A1 | | 10/2004 | Kang et al. | |
| 2005/0079201 | A1 | | 4/2005 | Rathenow et al. | |

FOREIGN PATENT DOCUMENTS

| WO | WO 00/64506 | * | 11/2000 |
| WO | WO 03/018083 A2 | | 3/2003 |
| WO | WO 03/018083 A3 | | 3/2003 |
| WO | 03/039612 | * | 5/2003 |
| WO | WO 03/070156 | | 8/2003 |
| WO | WO 2004/105826 A2 | | 12/2004 |
| WO | WO 2004/105826 A3 | | 12/2004 |
| WO | WO 2005/000740 | * | 1/2005 |

OTHER PUBLICATIONS

Gorman, Sean P, Antimicrobial Biomaterial Medical Devices, Business Briefings: Medical Device Manufacturing and Technology, (2002), pp. 1-4.*
Extended European Search Report for European Patent Application No. 09167016.6-1219, dated Sep. 28, 2009.
International Preliminary Report on Patentability from the International Preliminary Examining Authority for PCT/BE2005/000108, completed and mailed Jul. 4, 2006.
International Search Report for PCT/BE2005/000108, completed Dec. 22, 2005 and mailed and published Jan. 12, 2006.
Kuznicki et al., "A titanosilicate molecular sieve with adjustable pores for size-selective adsorption of molecules," *Nature* 412: 720-724 (2001).
Reply to the Written Opinion of the International Searching Authority for PCT/BE2005/000108, dated Mar. 28, 2006.
Written Opinion of the International Searching Authority for PCT/BE2005/000108, mailed Jan. 12, 2006.
European Patent Office Communication for related Application No. 09 167 016.6 dated Sep. 14, 2011 (2 pages).
European Patent Office Annex to the Communication for related Application No. 09 167 016.6 dated Sep. 14, 2011 (3 pages).

* cited by examiner

*Primary Examiner* — Scott Long
*Assistant Examiner* — Lyndsey Beckhardt
(74) *Attorney, Agent, or Firm* — Clark & Elbing LLP

(57) ABSTRACT

A coated implantable medical device is described, wherein the coating comprises a coating matrix and particles of one or more molecular sieves, preferably zeolite of zeogrid particles, optionally loaded with one or more bioactive agents. The coating matrix itself can function as a second drug-carrying interface. The coating comprising the molecular sieve material has an excellent biocompatibility and allows suitable drug delivery into the body of an animal, preferably a mammal and most preferably a human.

4 Claims, 11 Drawing Sheets

BIOCOMPATIBLE COATING OF MEDICAL DEVICES

CROSS-REFERENCE TO RELATED APPLICATIONS

This application is the U.S. National Stage of International Application Ser. No. PCT/BE2005/000108, filed Jul. 5, 2005, which, in turn, claims benefit of Great Britain Application Ser. No. 0414911.8, filed Jul. 5, 2004, and Great Britain Application Ser. No. 0425322.5, filed Nov. 17, 2004.

FIELD OF THE INVENTION

This invention relates to the coatings for the human and veterinary medical devices, which are to be introduced into or implanted in a human or animal body, and especially such devices as will come into contact with circulating blood supply and more particularly to those devices which provide drug release, e.g. devices incorporating biologically active, therapeutic or similar agents in said coatings. Further the present invention relates to methods of making the materials of such coatings and of applying such coatings to medical devices.

BACKGROUND

It has become a trend to treat a variety of medical conditions by introducing an implantable medical device partly or completely into the body cavity such as oesophagus, trachea, colon, biliary tract, urinary tract, vascular system or other location within a human or veterinary patient.

For example, many treatments of the vascular system entail the introduction of a device such as a stent, catheter, balloon, guide wire, cannula or the like. For instance classical treatments for artherosclerosis include medical therapies with balloon-dilatations optionally involving stent-implantation and coronary bypass surgery. Artherosclerosis is one of the most important causes of death in the Western world. Coronary artherosclerosis is the result of a progressive degeneration of the vessel wall which causes the occlusion of the arteries with different substances including lipids, cholesterol, calcium and different types of cells including smooth muscle cells and platelets. Classical treatments include medical therapies, balloon-dilatations optionally involving stent-implantation and coronary bypass surgery.

Balloon-dilatations or percutaneous transluminal angioplasty (PTA) is being applied more and more and consists of breaking up and/or removing already formed deposits along arterial walls using a balloon attached to a catheter that is introduced to a patient percutaneously and threaded through the arteries to the occluded site, where the balloon is inflated. An important limitation of this technique however is the high risk of re-closing (restenosis) of the treated artery. Thus, balloon-angioplasty does not always lead to a permanently opened artery. Though systemic drug therapy has been developed to reduce this restenosis reaction it has not shown convincing results, mostly because of unwanted side effects in other parts of the body while the concentrations in the blood vessel wall at the site of occlusion were too low to be effective.

In order to prevent the re-closing of the arteries, scaffolding devices called stents have been developed which are introduced into the lumen of the artery to keep them open. Unlike the balloon-catheter, the stent remains in the body as a permanent prosthesis.

Stents coatings have been developed for different purposes. Firstly, in order to reduce allergic or immunological reactions to the stent material, biocompatible polymers have been used to improve the biocompatibility of the stent. A coating substance may also add to the strength of the stent, or make its surface smoother, allowing easier introduction into the vessels.

The use of stents to permanently maintain the opening in the lumen of arterial walls has not completely eliminated the problem of restenosis. Apparently, introduction of the stent itself often causes damage to the inner lining of the vessel wall, inducing a 'reparatory' reaction leading to platelet aggregation and the migration of vascular smooth muscle cells into the arterial lumen, where they accumulate and cause occlusion of the vessel. While the accumulated platelets can produce inflammatory mediators, the damaged endothelium recruits monocytes and leukocytes to the injury site, further contributing to neointimal hyperplasia.

The problem of stent-induced restenosis has been addressed in different ways. Irradiation therapy has been suggested based on intravascular low-power red laser light (LPRLL), using a liquid sodium 186Re perrhenate solution as beta emitter, or potentially gamma radioactive stents made of platinum-iridium. Use of radioactive materials in intimate contact with body tissue over long periods is not preferred.

Alternatively, local drug delivery by the stents themselves has been suggested. Bare metallic stents can be used as a platform to deliver drugs locally where the stents struts enter the vascular wall providing a high drug concentration around the stent struts. Though bare stents can be loaded with a drug without using a carrier interface, the amount of drug loaded this way is low and the release curve fast and not controllable (De Scheerder et al. 1996, Coron Artery Dis 7(2):161-166). Most drug eluting stents therefore use a drug carrying interface, e.g. a coating. Coated stents can be loaded with a larger amount of drug and drug release can be better modified to obtain a more optimal drug release profile resulting in more prolonged effective tissue drug levels. Moreover, this form of drug-delivery is not limited to restenosis-inhibiting compounds.

A number of biocompatible materials suitable for the coating of implantable medical devices have been developed. More particularly, in the field of stent-coating several materials have been tested for drug delivery-characteristics either in animal models only or also in clinical trials, such as phosphorylcholine (PC), polylactide or polylactide copolymers and fluorinated polymethacrylates PFM-P75.

More recently elastomeric poly(ester-amide) (coPEA) polymers and poly-bis-trifluorethoxy phosphazene (PTFEP) have been shown to have the required biocompatibility characteristics and have been suggested as a candidate for local drug delivery. Using stacked layers of polymer it was been demonstrated that the pharmacokinetics of the drugs could be manipulated.

Different drugs have been tested using local delivery from stent coatings to reduce neointimal hyperplasia, including anti-proliferative, immunosuppressive, anti-thrombotic and anti-inflammatory drugs. Heparin has shown only limited benefits in clinical trials.

Use of poly(organo)phosphazene coating impregnated with the corticosteroid methylprednisolone was shown to result in a significantly reduced neointimal thickening over the long term (6 weeks) after stenting of pig coronary arteries (De Scheerder et al. 1996, Coronary Artery Disease 7(2):161-166). More recently, local delivery of a high dose of methylprednisolone from phosphatidyl choline-coated stents or PMF 75 spray-coated stents was found to effectively decrease inflammatory response and result in a significant reduction of neointimal hyperplasia.

Other new drugs also appear to be promising. Recent studies have evaluated these drugs as to their release kinetics, effective dosage, safety in clinical practice and benefit. These studies include trials on sirolimus or rapamycin (RAVEL, SIRIUS), Actinomycin D (ACTION), Tacrolimus (PRESENT), Placitaxel and derivatives (SCORE, ASPECT, ELUTE), dexamethason (EMPEROR), everolimus (FUTURE).

Estrogen inhibits intimal proliferation and accelerates endothelial regeneration after angioplasty. 17Beta-estradiol-eluting phosphorylcholine coated stents were found to be associated with reduced neointimal formation. Gene therapy on the vessel wall by local delivery of DNA has also been considered. Effective transfection of neointimal cells was demonstrated using plasmid DNA loaded Polylactic-polyglycolic acid (PLGA) as stent coating.

WO 03/035134 describes a stent coating composition comprising a biodegradable carrier and a bioactive component. The biodegradable carrier is either polymeric or non-polymeric and examples of non-polymeric carriers are vitamin E or derivatives thereof, peanut oil, cotton-seed oil, oleic acid- or combinations thereof.

One of the drawbacks of conventional means of drug delivery using coated medical devices however, is the difficulty in effectively delivering the bioactive agent over a short term (that is, the initial hours and days after insertion of the device) as well as over a long term (the weeks and months after insertion of the device). Another difficulty with the conventional use of stents for drug delivery purposes is providing precise control over the delivery rate of the desired bioactive agents, drug agents or other bioactive material.

In view of the potential drawbacks to conventional drug delivery techniques, there exists a need for a mechanism for controlling the release rate of the drugs for implantable medical devices to increase the efficacy of local drug delivery in treating patients. There is a need for a device, method and method of manufacture which enable a controlled localised delivery of active agents, drug agents or bioactive material to target locations within a body.

SUMMARY OF THE INVENTION

The present invention provides compositions for coating of implantable medical devices, which present a number of advantages over the prior art coatings. More particularly, the coating compositions of the present inventions are biocompatible and are suited for loading and controlled delivery of bioactive agents. Most particularly, the coating compositions of the present invention have been found to demonstrate an anti-restenotic effect per se, making them particularly suited for the coating of endovascular medical devices.

A first aspect of the invention thus relates to coating compositions for medical devices, most particularly implantable medical devices, i.e. devices which are to be introduced partially or completely into the human body. The coating compositions of the present invention comprise a coating matrix and particles of one or more molecular sieves. The particles of the one or more molecular sieves are either embedded within the coating matrix or are covered by the coating matrix.

According to a second aspect of the present invention, the coating compositions comprising a matrix and particles of one or more molecular sieves are used as drug delivery (and optionally drug storage) compositions. Thus, the present invention provides compositions for delivering therapeutic agents into the body of a mammal. The compositions of the invention are biocompatible and are preferably applied to an implantable medical device, such as a stent or a vascular or other graft sheath, among other configurations. The compositions may be used as coating for human and veterinary medical devices, especially devices that are to be introduced into or implanted in a human or animal body, especially such devices as will come into contact with circulating blood supply. Thus the compositions of the invention are particularly biocompatible with the endovascular environment.

According to a particular embodiment of the present invention, the coating composition comprises a coating matrix which is a hydrophobic matrix. Most particularly such a hydrophobic matrix is a cis-hydrogenated Omega-3 fatty acid.

According to the present invention, the coating composition comprises a coating matrix and particles of one or more molecular sieves. Most particularly such a sieve is a (ultra and/or super-microporous material, preferably a zeolite or a zeogrid, as described in the examples of this application.

According to a particular embodiment of the invention the particles and/or the coating matrix can optionally further comprise, one or more bioactive agents. According to a most particular embodiment of the present invention, the molecular sieve and optionally the coating matrix are loaded with the same or a different drug to be released. Further specific embodiments relate to the loading of hydrophilic drugs in the molecular sieve embedded in or covered by a hydrophobic matrix on the surface of an implantable medical device.

According to one embodiment of the present invention, the particles of the one or more molecular sieves or the matrix comprising the particles of the molecular sieves are present essentially only within structural cavities in the surface of an implantable medical device.

According to another aspect of the present invention, methods are provided for the controlled release of one or more bioactive agents from an implantable medical device. The controllable release is achieved by one or more of the following factors a) the combination of the molecular sieve with the matrix, b) the selection of the pores of the molecular sieve particles, or the selection of the size of the molecular sieve materials and c) the adjustment of the biosolubility kinetics of the matrix.

An object of present invention is thus to provide medical devices which are coated with a biocompatible coating composition, i.e. which results in minimal reactivity of the environment in which the medical device is placed. A further object of the invention is to provide a medical device which is coated with a coating composition which can be loaded with and which can release a suitable bioactive agent. Thus, according to the present invention, the implants are coated with a coating composition containing a means which acts as a drug reservoir and ensures drug release, preferably in a controlled manner. The present invention thus provides devices and methods for reliably delivering suitable amounts of one or more bioactive agents such as therapeutic agent or drug directly into a body portion during or following a medical procedure, so as to treat or prevent such conditions and diseases, for example, to prevent abrupt closure and/or restenosis of a body portion such as a passage, lumen or blood vessel or to prevent bacterial infection.

According to one embodiment of the present invention, the implantable device is a pitted stent. The surface of the pitted stent is perforated by holes or pits which is filled with the coating composition of the present invention to increase the load of therapeutic agent and/or to control its release. According to a particular embodiment the pitted stent is a radially expandable prosthesis with reservoirs made in the outer surface for containing therapeutic agents described in WO0166036 and EP1348405.

Yet a further aspect of the present invention relates to methods of making the coatings of the present invention and methods of applying the coatings of the present invention to implantable medical devices.

Yet another aspect of the present invention relates to methods for preventing adverse reactions to an implanted device, which methods comprise coating the device with a coating composition of the present invention comprising a coating matrix and particles of one or more molecular sieves, optionally loaded with a bioactive agent. More particular embodiments of the invention relate to methods for preventing restenosis upon implantation of an endovascular prosthesis, which method comprises coating the prosthesis with the coating compositions of the present invention prior to implantation. The invention further relates to the use of a coating matrix and particles of at least one molecular sieve, more particularly of a silicate molecular sieve material, most particularly of a zeogrid, in the coating of implantable medical devices for the sustained release of a bioactive agent.

DETAILED DESCRIPTION

The present invention relates to biocompatible coatings for implantable devices comprising a coating matrix and particles of one or more molecular sieves. According to a particular embodiment the coating matrix and/or particles are loaded with a bioactive agent.

The term "bioactive agent" is used herein to mean any agent such as a pharmaceutical agent or drug or other material that has a therapeutic effect. It thus includes, but is not limited to, chemical compounds, DNA, RNA, vectors comprising DNA or RNA, antibodies, etc. Alternatively the bioactive agent may be an agent for use in detection, e.g. a label, such as a contrast agent, a luminescent or fluorescent agent etc.

"Biocompatible" as used herein relates to the fact that it is well-tolerated in the body, i.e. that does not have a toxic or injurious effect on the biological system. However, depending on the application, requirements of compatibility may vary. Thus, in some situations biocompatibility may also imply the ability of a material to perform with an appropriate host response, i.e. which can interact with and in time be integrated into the biological environment. In this regard medical devices used for implantation into the cardiovascular system can be considered to have particular requirements. Thus, 'endovascular biocompatibility' and more particularly 'cardiovascular compatibility', when used to describe a material herein relates to the fact that the material does not, or only to a very limited extent, induce reactions which are typically observed in the endovascular system in response to the introduction of a foreign object and which are undesired for the appropriate functioning of the vessel and the medical device implanted therein. These reactions include and can be measured as damage of the vascular wall, inflammation, reduction of the lumen area, neointimal hyperplasia, and area stenosis.

The term "implant" or "implantable medical device" as used herein refers to any device which is intended to be introduced and optionally implanted into the human body, including devices used for implantation into vessels, ducts or body organs, such as a stent, catheter, canunula, vascular or arterial graft sheath, a device for implantation into the oesophagus, trachea, colon, biliary tract, urinary tract, orthopaedic devices etc.

A "stent" as used herein refers to an implantable medical device used to support a structure within the human or animal body, such as but not limited to the oesophagus, trachea, colon, biliary tract, urinary tract, vascular system or other location within a human or veterinary patient. A particular embodiment of the invention relates to a vascular stent, more particularly a stent for use in supporting coronary arteries.

A pitstent or pitted stent as used herein refers to a stent comprising (perforating) holes or non-perforating (pits) openings in its outer and/or inner surface.

The term "molecular sieve" as used herein refers to a solid with pores the size of molecules. It includes but is not limited microporous and mesoporous materials, ALPOs and (synthetic) zeolites, pillared or non-pillared clays, clathrasils, clathrates, carbon molecular sieves, mesoporous silica, silica-alumina (for example, of the M41S-type, with an ordered pore system), microporous titanosilicates such as ETS-10, urea and related host substances, porous metal oxides. Molecular sieves can have multimodal pore size distribution, also referred to as ordered ultramicropores (typically less than 0.7 nm) supermicropores (typically in the range of about 0.7-2 nm) or mesopores (typically in the range of about 2 nm-50 nm). A particular type of molecular sieves envisaged within the present invention are the silica molecular sieves, more particularly silica zeogrids and/or zeolites.

A "zeogrid" is a silica superstructure with a combination of super- and ultra-micropores and with an X-ray diffraction pattern typical of a layered structure, such as in FIG. 1 (see also Kremer et al. Adv. Funct. Mater. 2002, 12:286). Supermicropores have free diameters in the range of typically 7 to 20 Å, ultramicropores have free diameters of less than 7 Å, identifiable by Nitrogen-adsorption (Rouquerol & Rouquerol, Adsorption by powders and porous solids, 1999, Sing, Academic Press).

A "zeolite" can be defined as a crystalline material of which the chemical composition includes essentially aluminium, silicon and oxygen. Typically, zeolites are described as aluminosilicates with a three dimensional framework and molecular sized pores.

| Nomenclature of molecular sieves | | | | |
|---|---|---|---|---|
| Molecular sieves | | | | |
| Pore size | Microporous <20 Å | | Mesoporous 20-500 Å | |
| Composition | Al & Si aluminosilicate | Al & P aluminophosphate | Al & Si | Al & P |
| Name | zeolites | AlPOs | Mesoporous | |

The term 'matrix' as used herein refers to a material suitable for the coating of an implantable device, i.e. a material that is biocompatible and can be applied to the surface of an implantable device so as to obtain a coating.

The present invention is based on the observation that molecular sieves such as supermicroporous or ultramicroporous silicate material can be used in the coating of medical implants and is biocompatible. It has been observed that medical devices coated with the coating compositions of the present invention, when implanted in a porcine coronary vessel, did not result in a significant damage of the vascular wall, that no increased inflammatory reaction was observed, that there was no significant reduction of the lumen area, and that neointimal hyperplasia and area restenosis were not significantly increased compared to bare stents. To the contrary, it was observed that the use of molecular sieves, more particularly the use of silicate zeogrids resulted in less area stenosis than the control groups without the molecular sieves, indicating an anti-restenotic effect of the molecular sieve-comprising coating material.

The present invention is further based on the observation that molecular sieves, i.e. particles of porous material, more particularly (super/ultra) microporous silicate material, such as zeolites or zeogrids, can be loaded with a bioactive agent such as a drug, for instance, β-estradiol and can be used to ensure a controlled (i.e. sustained) release profile for the loaded bioactive agent (and thus act as a drug carrying interface).

A particular embodiment of the present invention thus relates to a coating composition of an implantable medical device comprising molecular sieve particles that comprise a bioactive agent or drug, wherein release of said drug is controlled. Controlled release as used herein refers to a release that is adjusted to the requirements of the purpose of the drug. For instance, controlled release can refer to sustained release, i.e. release that does not occur immediately, e.g. more than 25% within the first 24 hours. Controlled release of a bioactive agent comprised in a zeogrid or zeolite embedded in a matrix can be demonstrated in an in vitro setting as shown in the examples below. Controlled release of one or more bioactive agents is obtained by modulating one or more of the following a) the structure of the molecular sieve particles (pore, structure size), b) the properties of the matrix material (biostability/biodegradability, density, thickness) and c) the nature of the loaded bioactive agents relative to the nature of the matrix material (hydrophilicity).

As indicated below, a combined release pattern (e.g. both immediate release from the matrix and controlled release from the molecular sieve particles embedded therein) is also envisaged within the context of the present invention.

Moreover, the use of molecular sieves significantly increases the drug-loading capacity of the medical device. Application of the present invention to medical devices with structural cavities can further improve the loading capacity of the medical device. For instance, a pitted stent coated by a hydrophobic matrix (optionally loaded with a drug) and a zeolite or zeogrid loaded with a drug has an increased drug loading capacity as compared to classic (non-pitted stent) stents coated by a hydrophobic matrix loaded with drug or even a pitted stent coated by a hydrophobic matrix loaded with drug. Thus the present invention provides implantable devices which allow increased (i.e. over longer period of time or of higher amounts) of drug delivery.

According one aspect of the present invention, the molecular sieves are thus used as reservoirs and delivery systems for bioactive agents and can be selected so as to ensure controlled release of the bioactive agents. The size of the pores within the molecular sieve can be selected so as to ensure a faster or slower release of the bioactive agent. Zeogrid and MCM-22 are particular suitable molecular sieves for the use in present invention. The preparation and characterisation of MCM-22 samples has been described by S. Laforge, et al. Microporous and Mesoporous Materials Volume 67, Issues 2-3, 6 Feb. 2004, Pages 235-244. U.S. Pat. No. 4,954,325 (1990) discloses that MCM-22 contains three independent types of pores: two-dimensional sinusoidal channels (4.1×5.1 Å), large supercages (7.1 Å, 18.2 Å height) accessible through 10-MR openings (4.0×5.5 Å) and large pockets on the external surface (7.1 Å, 7 Å depth). Alternative molecular sieves envisaged within the context of the present invention include but are not limited to silicalite, ZSM-5 zeolites, mordenite, zeolite L, zeolite X, zeolite Y, zeolite LSX, MCM-41 zeolites, silicoaluminophosphates (SAPOs), zeolite beta, zeolite omega, ZSM-5, ZSM-12, MSM-36, MCM-49 . . . etc.

Molecular sieves can be synthesised with pore size suitable for a particular release profile and optionally a particle size suitable for embedding into the matrix and/or incorporation in the cavities of the prosthesis.

Zeolites, such as MFI (silicalite-1, ZSM-5, TS-1), hydroxysodalite, LTA (zeolite A), MTW (ZSM-12), FAU, BEA (zeolite beta), LTL (zeolite L), and AFI (ALPO4-5), with particle size in the nano-scale range known from the prior art (JunPing Dong et al. Microporous and Mesoporous Materials, Volume 57, Issue 1, 2 January 2003, Pages 9-19).

The pore size of molecular sieves can further be influenced by the nature of the templating molecules in the synthesis of the mesoporous or microporous composition of this invention. The addition of swelling agents to the synthesis mixture can further affect the pore size of the resulting molecular sieve. Zeolites with different pore size have been well characterised and described by Martin David Foster in "Computational Studies of the Topologies and Properties of Zeolites", The Royal Institution of Great Britain, Department of Chemistry, University College London, A thesis submitted for the degree of Doctor of Philosophy, London, January 2003. Suman K. Jana et al Microporous and Mesoporous Materials Volume 68, Issues 1-3, 8 Mar. 2004, Pages 133-142 describes how pore size can be controlled in molecular sieves, particular in Mesoporous MCM-41 and SBA-15 molecular sieves by the of different organic auxiliary chemicals such as methyl-substituted benzene (1,3,5-, 1,2,4- or 1,2,3-trimethylbenzene), isopropyl-substituted benzene (1-, 1,3-di- or 1,3,5-tri-isopropylbenzene) and alkane (octane, nonane, decane, tridecane, hexadecane or eicosane) as auxiliary chemicals.

Synthetic zeolites are currently produced as powders of micron size crystals and compacted into millimeter size extrudates or other forms of pellets for applications as adsorbents and catalysts. In many of these applications, mass and heat transfer properties could potentially be improved by forming the zeolite in a different way. Research in this area led already to significant achievements. Examples of alternatively structured zeolite matter reported in recent literature are for example delaminated zeolites (A. Corma et al, *Nature* 1998, 396, 353.), supported zeolite films and membranes (J. Caro et al, *Microporous Mesoporous Mater.* 2000, 38, 3.), mesoporous-microporous hybrid structures with microporosity in walls of ordered mesoporous materials (Z. Zhang et al, *J. Am. Chem. Soc.* 2001, 123, 5014.) and nanosized zeolites such as those synthesized in confined space (I. Schmidt et al, *Inorg. Chem.* 2000, 39, 2279). The common property of these alternative zeolite materials is that at least in one dimension, the zeolite body is nanosized.

According to a particular embodiment of the present invention, zeolites are used wherein all or part of the ion-exchangeable ions have been replaced with ammonium ions or metal ions (as described in U.S. Pat. No. 4,938,958).

According to a particular embodiment of the invention the molecular sieve particles contain more than one bioactive agent. Before mixing in the coating, the molecular sieve (e.g. microporous or mesoporous) particles are loaded with different drugs to obtain multiple drug-release. Alternatively, different layers of coating with microporous or mesoporous particles that contain different drugs can also be applied. The drug-release from mesoporous or microporous particles, can also be combined with drug release from the coating that contains the mesoporous or microporous particles.

According to the present invention the molecular sieves can either be embedded in a polymeric or non-polymeric matrix, that is loaded onto to the implantable device or can be glued to the surface of the implantable medical device and covered by a matrix, which can optionally further influence the release of the loaded bioactive agent. Examples of biocompatible glues for use in the context of the present invention include fructose, glucose, sucrose, saccharose, lactose, maltose, dextrins and celluloses. Also, oils, fats, fatty acids or cis-hydrogenated oils are envisaged as gluing products. Subsequently, the glued layer of molecular sieve particles can be covered by a biocompatible matrix.

The coating compositions of the present invention comprise particles of one or more molecular sieves and a coating matrix.

The coating matrix can be a hydrophobic matrix and consist essentially of (i.e. consist in at least 80% of) an oil or a combination of oils such as, but not limited to, a marine animal derived oil, a terrestrial animal derived oil, a plant-derived oil, a mineral oil and a silicone oil, or a combination of one or more of these oils. The matrix can be an oil (or a combination of oils) selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojova oil.

The matrix can also be an oil selected from the group consisting of omega-3 oil and omega-6 oil. According to a particular embodiment of the invention, the matrix additionally comprises a solidifying agent. Additionally or alternatively, the matrix used according to the present invention may be a totally or partially chemically hardened oil or fat, in particular a hydrogenated oil or fat.

Particular embodiments of the chemically hardened oil or fat may comprise unsaturated fatty acid chains but be substantially free of trans-isomers of unsaturated fatty acids, i.e. a cis-hydrogenated fatty acids. Thus, according to a particular embodiment the coating matrix of the present invention comprises at least 20% of one or more cis-hydrogenated fatty acids. The term 'cis-hydrogenated fatty acid' (CHFA) as used herein relates to fatty acid compounds which are essentially free of trans-unsaturated double bonds. Fatty acid compounds comprise esters, mono-, di- and triglycerides, phospholipids, glycolipids, diol esters of fatty acids waxes and sterol esters, more particularly oleic acid, stearic acid or any mixture thereof. Most suitable fatty acids are triglycerides having a length of 4 to 24 C. The cis-hydrogenated fatty acids which are used for the coating of medical devices in the context of the present invention are, according to one embodiment selected from mono-, di- or triglycerides or esters thereof. Most particularly, they are made up of between 20% and 95% triglycerides. The fatty acid can originate from vegetable oils, such as, particularly soybean, sesame seed and peanut oil, but also including sunflower seed, cottonseed, corn, safflower, palm, rapeseed or animal oils, such as fish oils and mixtures of such oils. Oils of mineral origin or synthetic fats can also be employed as long as they are sufficiently biocompatible and/ or non-toxic. According to a particular embodiment of the invention, the cis-hydrogenated fat can comprises one or more cis-hydrogenated omega-3 fatty acids, particularly, but not limited to cis-hydrogenated forms of eicosapentaenoic acid (EPA) and docosahexaenoic acid (DHA). According to a more particular embodiment of the invention, the fatty acid comprises a substantial amount of omega-3 fatty acids. Oils obtained from cold water fish are generally rich in omega-3 fatty acids. Cod liver oil comprises about 20% by weight of omega-3 fatty acids.

Fatty acids with reduced level of trans-unsaturated double bonds can be obtained by influencing the hydrogenation conditions of oils to reduce the amount of trans-isomers formed (Puri P. J Am Oil Chem Soc 55(12):865-), by use of metal alloy catalysts or adding modifiers or ammonium compounds (U.S. Pat. No. 4,307,026). In WO 98/54275, however, a process is described which enables the significant reduction or elimination of trans-unsaturated fatty acid compounds from a substrate containing cis and trans isomers by means of a zeolite material.

Additionally or alternatively, the matrix may be enriched with natural or biologically safe fatty acids and particularly be enriched with DHA (22: 6n-3 docosahexaenoic acid) and/ or EPA (20: 5n-3; Eicosapentaenoic acid) which are known to have significant antithrombotic and anti-atherioisclerotic effects and have been known to significantly block mitogenic effects of serotonin. Alternatively the matrix is a silicon, a silicon elastomer or a silicon blend. These silicones may comprise one or more adjuvant polymers. Polymers are biocompatible (i.e., not elicit any negative tissue reaction or promote mural thrombus formation) and degradable, such as lactone-based polyesters or copolyesters, e.g., polylactide, polycaprolacton-glycolide, polyorthoesters, polyanhydrides; poly-aminoacids; polysaccharides; polyphosphazenes; poly (ether-ester) copolymers, e.g., PEO-PLLA, or blends thereof. Nonabsorbable biocompatible polymers are also suitable candidates. Polymers such as polydimethyl-siloxane; poly (ethylene-vinylacetate); acrylate based polymers or copolymers, e.g., poly(hydroxyethyl methylmethacrylate, polyvinyl pyrrolidinone; fluorinated polymers such as polytetrafluoroethylene; cellulose esters. Examples of suitable biocompatible polymers or polymer combinations include but are not limited to poly(vinyl pyrrolidone)/cellulose esters, poly(vinyl pyrrolidone)/polyurethane, poly(methylidene maloleate), polylactide/polyglycolide copolymers, poly(ethylene glycol) copolymers, poly(ethylene vinyl alcohol) and poly(dimethylsiloxane)-based systems.

The matrix can be covered on the surface of the implantable medical device or can be introduced into holes or reservoirs made (for instance drilled) in the implantable medical device. According to the invention the matrix comprises or envelopes molecular sieves.

According to one embodiment of the present invention, the hydrophobic matrix comprising the particles of porous material, is itself additionally loaded with a bioactive agent or drug, either the same drug or a different drug from that/those comprised in the porous material. This coating thus functions as a second drug-carrying interface. According to one particular embodiment of the present invention, the particles of the molecular sieve hold a hydrophilic drug, while the coating matrix holds a hydrophobic drug. According to a particular embodiment the particles of the molecular sieve comprise one or more non-lipophilic drugs that are not particularly suited for local drug-delivery from the coating, e.g. in the case of a cis-hydrogenated omega-3-fatty acid-based coating. The combination of both release systems is particularly suitable to obtain a dual release of the same or a different drug and can be used to optimise drug release, e.g. for counteracting unfavourable body reactions on the implant.

According to a further embodiment, the matrix can be covered by a second layer comprising a biocompatible polymer or a hydrophobic solution, which can be selected from the polymers described above. Such an additional layer can be used as a third drug carrying interface.

According to one embodiment of the present invention, the matrix comprising the molecular sieves is applied to an implantable medical device comprising structural cavities in its (inner and/or outer) surface. According to this embodiment the matrix comprising the molecular sieves can be present both on the surface and in the structural cavities therein. Alternatively, the matrix is present essentially only in the structural cavities in the surface of the implantable medical device. This can be achieved, removing the excess coating material on the surface of the prosthesis in between the holes or pits of said device, after the latter have been filled, e.g. by wiping off or cleaning the coating material and thus obtaining an essentially non-surface-coated stent. Optionally, this stent is then further coated with another second coating matrix (which is selected from the coating matrices described herein). Alternatively, selective filling of only the structural cavities with the matrix can be achieved by selectively filling the pores using micro-injection techniques.

According to a particular aspect, the present invention relates to the use of a coating for local drug-delivery for further optimisation of the drug release from the medical device and for controlling the release in accordance with the unfavourable body reaction.

A wide variety of drugs is envisaged for which local delivery from the coating of an implanted medical device would be beneficial. More particularly, in the context of implants, local delivery of anti-inflammatory and immunomodulatory drugs has generally been demonstrated to be beneficial. A wide range of drugs can be impregnated and released by the coating of the present invention. In the application of the invention to drug-eluting stents (also referred to as DES), the therapeutic agents envisaged suitable include but are not limited to corticosteroids such as dexamethasone and methylprednisolone, drugs used to prevent transplant rejection, such as cyclosporin, sirolimus, tacrolimus and everolimus, antiproliferative drugs such as vincristine, doxyrubicine, paclitaxel and actinomycin and metalloprotease inhibitors, such as batimastat. Other suitable therapeutic agents include sodium heparin, low molecular weight heparin, hirudin, argatroban, forskolin, vapiprost, prostacyclin and prostacyclin analogues, dextran, D-phe-pro-arg-chloromethylketone, dipyridamole, glycoprotein Ib/IIb/IIIa platelet membrane receptor antibody, recombinant hirudin, thrombin inhibitor, angiopeptin, angiotensin converting enzyme inhibitors, calcium channel blockers, colchicine, fibroblast growth factor antagonists, histamine antagonists, HMG-CoA reductase inhibitor, methotrexate, monoclonal antibodies, nitroprusside, phosphodiesterase inhibitors, prostaglandin inhibitor, serotonin blockers, steroids, thioprotease inhibitors, triazolopyrimidine, PDGF antagonists, alpha-interferon, genetically engineered epithelial cells, and combinations thereof. Alternatively, the therapeutic agent for use in the context of the present invention can be a nucleic acid, encoding one or more therapeutic agents such as those described above or encoding a molecule which, when present in the cells of the tissues surrounding the implantable device, has a therapeutic effect. According to yet another embodiment of the present invention the therapeutic agent can be a composition comprising cells, such as (genetically modified) epithelial cells.

According to the present invention the bioactive agents used for loading into the molecular sieves can be either hydrophilic or hydrophobic.

Bioactive agents for loading into the hydrophobic matrix according to one embodiment of the present invention are preferably hydrophobic. Hydrophilic drugs may be coupled to the natural fatty acids to render them hydrophobic (lipophilic). DHA is a 22 carbon naturally occurring which is particularly suitable to this end as this unbranched fatty acid can be used to attached drugs. DHA can for instance be attached via the acid group to hydrophilic drugs rendering these drugs more hydrophobic (lipophilic). For instance covalent conjugation of a natural fatty acid to paclitaxel is well known in the art (Bradley et al., Clin Cancer Res. 2001 October; 7(10):3229-38) and procedure to link fatty acids to amino acids, peptides, drugs and other compounds have been described in EP0712389.

According to a particular embodiment of the present invention, the bioactive agent comprised within the pores of the molecular sieve is not an inorganic anti-microbial agent, more particularly not a metal ion, or a metal salt.

Methods for obtaining a hydrophobic carrier or matrix are known to the skilled person. Such a method for obtaining an hydrophobic carrier can be mixing a hydrophobic solvent with a solidifying agent at a temperature above its melting temperature so as to obtain a mixture and cooling the mixture. Such mixture may for instance contain 50-10 percent of said the hydrophobic solvent such as marine animal derived oil, terrestrial animal derived oil, plant-derived oil, mineral oil or silicone oil and 10-50 percent of a solidifying agent by weight.

A particular method for obtaining an hydrophobic carrier can be mixing a hydrophobic solvent with a solidifying agent whereby both the hydrophobic solvent and the solidifying agent are brought to a temperature above the melting temperature of the solidifying agent.

Such solidifying agent can be selected from the group consisting of at least one long chain fatty alcohol having at least 15 carbon atoms in its carbon backbone and at least one fatty acid, having at least 18 carbon atoms in its carbon backbone.

The solidifying agent can be agents selected from the group consisting of at least one long chain fatty alcohol having at least 15 carbon atoms in its carbon backbone, at least one fatty acid having at least 18 carbon atoms in its carbon backbone, an agent which has at least one alkyl group side chain in its carbon backbone, of an agent which has at least one alkyl group side chain in its carbon backbone wherein said carbon backbone of said fatty acid or said fatty alcohol has at least one hydroxyl group at position α and β, an agent which has at least one alkyl group side chain in its carbon backbone wherein said carbon backbone of said fatty alcohol has at least one hydroxyl group at position α and β, an agent which has at least one alkyl group side chain in its carbon backbone, wherein said carbon backbone of said fatty acid or said fatty alcohol has at least one hydroxyl group at positions 8-14 and an agent including a 12-hydroxy fatty acid.

The hydrophobic solvent used to make the hydrophobic matrix can be an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojova oil, preferably it includes an oil selected from the group consisting of omega-3 oil and omega-6 oil The present invention relates to the coating of implantable medical devices. A particular embodiment of the invention relates to an implantable medical device which is a vascular stent, more particularly a stent for use in supporting coronary arteries. Most commonly the stents are made out of metal or metal alloy, such as titanium, tantalum, stainless steel, or nitinol. According to a particular embodiment of the present invention the implantable device comprises one or a plurality of structural cavities, i.e. (perforated) holes or (unperforated) pits, which can be of different shapes including but not limited to a shape wherein the width is essentially the same as its length, (e.g. such as essentially round, square, polygonal) or a longitudinal shape wherein the length is more than twice the size of the width, (e.g. grooves or slits). In the case of hollow implantable medical devices, such as stents, the cavities can be located on the inner and/or outer surface of the device. Examples include but are not limited to the designs such as described in WO 98/36784, WO 01/93781, and WO02/32347. A particular embodiment of the present invention is a stent comprising struts with tiny laser-drilled holes throughout the stent, such as described in WO0166036 and EP1348405. More particularly, the implantable medical device can be a radially expandable prosthesis.

Different stents designs have been described in the art which are suitable for coating, optionally with drug-delivering compositions. Particularly suited in the context of the present invention are the stent designs described in U.S. Pat. No. 6,562,065, which relates to pitted stents or stents comprising laser drilled holes for drug wells, and U.S. Pat. No. 5,728,150 which relates to a microporous prosthesis. The coating compositions of the present invention can be applied to the whole stent and/or be used to fill the pits of the stent, optionally carrying particular therapeutic agents as described below. Other examples of suitable stents include but are not limited to those described in WO02/060351, WO03/082152, WO 03/079936, WO 03077802, WO 03072287, WO 03/063736, WO 03061528, WO 03/059207, WO 03/057078. These moreover include stents which are available commercially and/or have been tested in clinical trials including but not limited to the NIRx® stent (Bostn Scientific, Natick, Mass.), Cordis Bx Velocity®, Cook V-Flex plus®, S-Flex® and ChromoFlex® stent, Gianturco-Z®, Gianturco-Roche Z®, and Gianturco-RoubinII® stent.

According to a particular embodiment of the present invention, the coating matrix comprises cis-hydrogenated fatty acids. As these cis-hydrogenated fatty acids do not contain trans-unsaturated fatty acids, which have been demonstrated to be a potential health hazard, these fatty acids are particularly biocompatible. Coatings essentially comprising fatty acids moreover have the advantage that they are less likely to crack during expansion of the stent during fabrication, implantation and use. This also implies that no harmful fragments will be released from the coating in the body. Fatty acid coatings can result in a smooth layer, minimising the chances of damage to the surrounding tissues in the body, e.g. the endothelium in the case of a vascular stent.

The physicochemical properties of fatty acids strongly depend on the chemical structure of the fatty acid residues and more particularly on their chain length and the amount of double bonds present. According to the present invention, the coating of the medical device has a wax-like (non-fluid) consistency, which is maintained within the body. Thus, the melting point of the fatty acid coating should be above body temperature, i.e. above 38° C., particularly between 38° C. and 52° C., more particularly above 40° C. and below 50° C., e.g. between 40.6° C. and 47.6° C. By selecting the melting temperature of the coating composition to be above body temperature, it is ensured that the properties of the coating material are maintained within the body. This is of importance not only with regard to the interaction of the coating of the medical device per se with its environment within the body, but is also necessary to maintain an even prolonged release of therapeutic agents.

Hardening by hydrogenation is a common process to increase the melting profile of fatty acids. Hydrogenation can be partial or result in complete saturation of all double bonds. One particular way of obtaining the appropriate properties of the fatty acids coating composition of the present invention, is by incomplete hydrogenation. Thus, in accordance with a particular embodiment of the present invention, the melting point of the fatty acid is raised to above body temperature by controlled incomplete trans-free hydrogenation. Incomplete hydrogenation is a well-described flexible process whereby the nature of the products is determined by the nature of the starting material, the extent of hydrogenation and the selectivity. These parameters are controlled by the process conditions and the nature of the catalyst used (Gunstone F. 1999, Chapter 4: "Processing of Fatty Acids and Lipids", in "Fatty Acid and Lipid Chemistry", Aspen Publishers Inc., Gaithersburg, Md.). The process of hydrogenation can be monitored by tracking the amount of hydrogen consumed, by iodine value, the refractive index, by measuring the solid fatty acid content by NMR, measuring the solid fat index by dilatometry, determination of the slip melting point and/or gas chromatography of the methyl esters. With the hydrogenation processes used industrially, isomerisation of the carbon-carbon double bonds in the fatty acid residues occurs, beside the saturation of double bonds by the addition of hydrogen. Thus, even if the starting material does not contain any trans-isomers (as is the case of fatty acids from some biological origins), hydrogenation by means of metal catalysts will inevitably result in cis/trans isomerisation. However, using the method as described in WO 98/54275, hydrogenation can be carried out with selective adsorption of trans-isomers, ensuring an essentially trans-free cis-hydrogenated fatty acid composition.

Hence, it is a particular aspect of the present invention to prepare a coating material or a component of a coating material for a human or veterinary medical device, especially a device which is to be introduced into or implanted in a human or animal body, especially such a device as will come into contact with circulating blood supply and more particularly to a device which provides drug release, e.g. a device incorporating biologically active, therapeutic or similar agents in the coating, by firstly providing a fat or oil with a melting point below 37° C. and to trans-free hydrogenate such oil or fat to raise the melting point, e.g. to greater than 40° C. and less than 50° C. Ideally, the coating should not be molten at body temperature. The hydrogenation process is well characterised and is well suited to targeting the melting point range. In particular, natural materials such as fats often have three states close to the melting point: a higher temperature state in which the material is molten, a lower temperature state in which the material is recognisable solid and an intermediate or "thermoplastic" state in which it exhibits some solid and plastic properties. It is particularly preferred if the coating is in a thermoplastic state when in contact with body tissue, i.e. at or near the blood temperature. In addition, drug and excipient loadings may affect the thermo mechanical properties of the coating, particularly when the drug is a lipophilic liquid. In accordance with a further aspect of the present invention trans-free incomplete hydrogenation of the starting material is so selected and controlled that the final drug/excipient coating material mixture is in a thermoplastic state at body temperature, e.g. in the range 32 to 43° C., i.e. not in a liquid state in this range.

Further, it is a particular aspect of the present invention to control the thermo-mechanical properties of the coating materials so as to determine, select or set a drug elution profile by trans-free hydrogenation of an oil or fat, especially a cis-hydrogenated fatty acid composition.

Additionally or alternatively the desired consistency of the fatty acid coating composition can be influenced by the chain length of the fatty acids. The melting point of fatty acids increases with the number of carbon atoms (e.g. Butyric 7.9° C. (4c), Lauric 44.2° C. (12c), Stearic 69.6° C. (18c), Behenic 79.7° C. (22c)). Moreover odd chain fatty acids usually melt at a lower temperature than do the even chain acids containing one less carbon.

The desired consistency of the fatty acid coating composition can also be obtained by mixing of different components.

For instance, triglycerides, which correspond to a glycerol attached to three fatty acids by separate ester bonds) can have different combinations of different fatty acids. By combining fatty acids of different chain lengths and number of double bonds, the desired melting point can be obtained.

According to the present invention, compounds comprising cis-hydrogenated fats are used for the coating of implantable medical devices. The term coating as used herein can optionally refer to the application of a uniform layer over all or part of the medical device. Different methods of applying coatings are envisaged within the context of the invention, including dip coating, inkjet printing, painting and spray coating. According to a particular embodiment the cis-hydrogenated fats are mixed with a solvent, such as ethanol, where after the medical device is dipped into the oil/ethanol solution. The solvent is then evaporated under a heated airflow. Moreover, according to the present invention, different layers of cis-hydrogenated fats of the same or different composition can be applied, optionally separated by intermediate layers. This can be of interest for the sequential release of drugs (see below).

A particular procedure for coating intraluminal prosthesis with a fat or an oil comprises the following steps:
1) Cleaning (for instance by sonicating in 3% Isopanasol and then in deionised (DI) water), degreasing (for instance by acetone) and drying of the prosthesis
2) Dipping of the prosthesis in a sodium bicarbonate solution (for instance 30 seconds) and air-dry
3) Making a solution or an emulsion of a biocompatible oil and a solvent of for example pure ethanol
4) In this solution or emulsion a therapeutic agent can optionally be dissolved.
5) Applying to the prosthesis body of the therapeutic agent containing the oil/solvent emulsion using dip coating or spray coating or any other coating method. The prosthesis can be previously coated with zeolites or zeogrids, which have optionally been loaded with one or more therapeutic agents; alternatively these are introduced into the emulsion of step 3.
6) Air dry till the solvent is evaporated
7) Eventually repeat these previous steps multiple times
8) Use the prosthesis immediately or further air dry the prosthesis in a sterile laminar flow.
9) After drying the coated prosthesis can be sterilised. Either with ethylene oxide or gamma irradiation.

Additionally or alternatively, coating of a medical device can refer to the filling up of particular structures in the structure of the medical device, for instance the filling up of pits or grooves on the exterior (i.e. the side in contact with the body structure to be supported) of the medical device.

Other components can be added to the coating comprising the cis-hydrogenated fat of the invention, such as, but not limited to anti-oxidants (e.g. tocopherol) and solvents (which are optionally removed before use). In the coating of the present invention, the content of the cis-hydrogenated fats is not specifically limited, but is preferably 20-100% by weight, more preferably 70-100%.

According to the present invention the loading capacity of the cis-hydrogenated fat coatings for the drugs will be dependent on the hydrophilicity characteristics of the drug. It has been shown that lipophilic drugs have a higher solubility in the cis-hydrogenated fatty acids and a higher maximal drug loading capacity than hydrophilic drugs in coronary vascular wall (Bennett M R. In-stent stenosis: pathology and implications for the development of drug eluting stents. Heart. 2003; 89; 218-224). The cis-hydrogenated fat-based coatings are shown to potentially release about 20% of a therapeutic agent within 24 hours, allowing a fast loading of the injured tissue surrounding the stent strut. Local tissue drug concentrations rise quickly, and reach effective tissue drug concentrations within 24 hours to prevent the pathologic reactions after stent implantation.

The present application further demonstrates that the coating with cis-hydrogenated fats can provide a drug release curve characterised by a 20% of total drug amount released within 24 hours, 50% within one week, and 80% within four weeks. These release characteristics are well correlated with the pathologic processes induced by stent implantation. In a porcine model, after stent implantation, acute pathologic reactions (thrombus formation, inflammation) happen within five days, and sub acute reactions (smooth muscle cell proliferation) happen within four weeks. Thus, the drug release rate using the cis-hydrogenated fat-based stent coating is appropriate, from a therapeutic point of view. It is furthermore demonstrated that for some drugs a prolonged drug release rate over 6 weeks can be obtained.

The provision of several layers of coatings with cis-hydrogenated fats of the same or different compositions allows the modulation of the release of one or several drugs from the stent. In particular, the thermo mechanical properties of each layer may be controlled, selected or determined by the degree of trans-free incomplete hydrogenation of the material of each layer so as to achieve a specific drug eluting profile for each layer. Alternatively, the coating with cis-hydrogenated fats of the present invention can be combined with other bio-degradable coatings to ensure different release rates of one or more drugs from the coating.

The amount of therapeutic agent to be included in the coating of the stent will be determined by the therapeutic effect envisaged and the release curve of the therapeutic agent from the coating. Generally, for stents coated over their entire surface, the therapeutic agent will be present in the coating in an amount ranging from about 0.01 mg to about 10 mg and more preferably from about 0.1 mg to about 4 mg of the therapeutic agent per $cm^2$ of the gross surface area of the stent. "Gross surface area" refers to the area calculated from the gross or overall extent of the structure, and not necessarily to the actual surface area of the particular shape or individual parts of the structure. In other terms, about 100 micrograms to about 300 micrograms of therapeutic agent per 0.002 cm of coating thickness may be contained on the stent surface.

The evaluation of stents with a coating that contains (drug-loaded) zeolites or zeogrids can be performed in an animal model, such as a porcine coronary model.

Stent implantation in the right coronary artery, left anterior descending or left circumflex can be performed according to the method described by De Scheerder et al. in "Local angiopeptin delivery using coated stents reduces neointimal proliferation in overstretched porcine coronary arteries." J. Inves. Cardiol. 8:215-222; 1996, and in "Experimental study of thrombogenicity and foreign body reaction induced by heparin-coated coronary stents." Circulation 95:1549-1553; 1997. The guiding catheter is used as a reference to obtain an over-sizing.

The evaluation can include both an acute study and a chronic study. In the acute study, control bare stents, CHFA-coated stents, stents coated with drug-loaded CHFA, stents coated with CHFA that contains molecular sieves and stents coated with CHFA that contains drug-loaded molecular sieves are randomly implanted in coronary arteries of pigs. Pigs are sacrificed after 5 days to evaluate acute inflammatory response and thrombus formation. In the chronic study, control bare stents, CHFA-coated stents, stents coated with drug-loaded CHFA, stents coated with CHFA that contains molecular sieves and stents coated with CHFA that contains drug-loaded molecular sieves are randomly implanted in coronary arteries of pigs. Pigs are sacrificed after 4 weeks to evaluate peri-strut injury and in-stent neointimal hyperplasia.

Different parameters can be taken into consideration. Optionally, quantitative coronary angiography can be performed, before, immediately after stenting and at sacrifice using the Polytron 1000®-system. The Polytron has earlier been validated in vitro and in vivo with a metal bar as a calibration device. The diameter of the stented vessel segment is measured. The degree of over-sizing is expressed as balloon/artery thickness ratio. Stent recoil is measured as:

$$\frac{balloon + stent - stent}{balloon + stent}$$

To evaluate histopathology and morphometry, the pigs are sacrificed and the stented coronary segments are carefully dissected together with an 1 cm minimum vessel segment both proximal and distal to the stent after pressure fixation using a 10% formalin solution at 80 mmHg. The segment can be fixated in a 2% formalin solution. The sections are embedded in plastic and stained with hematoxylin-eosin, elastica von Gieson, PTAH and Mason's trichrome stain for light microscopic examination.

Damage of the arterial wall can be graded as:
  no disruption of the elastic membranes,
  disruption of the internal but not the external elastic membrane, or
  disruption of both elastic membranes.

Neointimal proliferation within the stented vessel segments can visually graded as:
  presence of a thin fibromuscular layer covered by new endothelium without noticeable
  narrowing of the lumen.
  neointimal proliferation leading to vessel lumen narrowing estimated to be less than 50%, or
  neointimal proliferation leading to vessel lumen narrowing estimated to be greater than 50%.

In addition, the predominant histological events (organisation of thrombus, histiolymphocytic reaction, fibromuscular reaction) leading to the luminal obliterations can be carefully examined.

Morphometric analysis of the coronary segments harvested can be performed using a computerised morphometry program (Leitz CBA 8000).

Measurements of maximal intimal thickening, the area within the lumen (lumen area) and inside the internal elastic lamina (intimal area) and external elastic lamina are performed on the arterial sites, visually appreciated as being the most proliferative.

BRIEF DESCRIPTION OF THE FIGURES

The following examples, not intended to limit the invention to specific embodiments described, may be understood in conjunction with the accompanying Figures, incorporated herein by reference, in which.

EXAMPLES

Example 1

Production of Zeogrids

An alternative approach to synthesize nanoscopically arranged molecular sieve material is reported.

Figure 1:
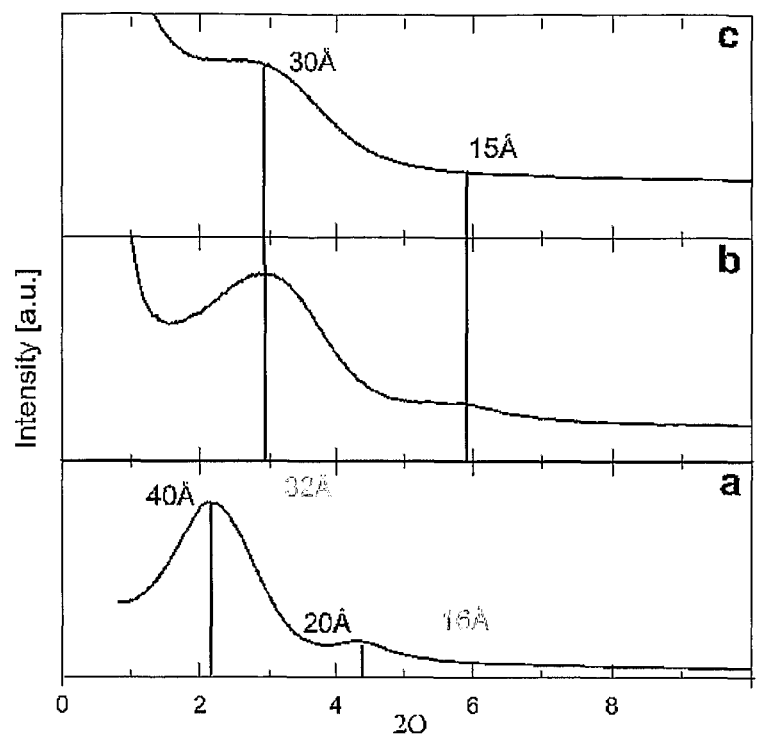
FIG. 1: XRD pattern of precipitate (a), of intermediate product from the calcination (b) and of final zeogrid (c) prepared using CTMABr (black trace) and DTMABr (grey trace) surfactants.

A suspension of Silicalite-1 type zeosil nanoslabs was prepared following a recipe from literature (C. E. A. Kirschhock et al, *Angew. Chem. Int. Ed.* 2001, 40, 2637; R. Ravishankar, et al, *J. Phys. Chem. B* 1999, 103, 4960). This nanoslab suspension was diluted with ethanol. Saturated solution of cetyltrimethylammoniumbromide (CTMABr) in ethanol was slowly added to the stirred suspension until a white precipitate formed. The precipitate was recovered by filtration, washed with ethanol and dried. The XRD pattern of the precipitate (FIG. 1a, black trace) revealed the presence of a layered compound showing first and second order diffraction and having a repeat distance of 4.0 nm. The precipitate was heated under flowing oxygen gas to 150° C. and kept under those conditions for 7 days. The sample was cooled to ambient temperature. At this intermediate stage of the calcination, the compound had a brownish color. Part of the product was kept aside for characterization, the remaining part was heated under a flow of nitrogen gas to 400° C. for 1 day and then cooled to 150° C. The sample was black owing to carbonaceous residue left after pyrolysis of the organic molecules. In the last step of the calcination procedure using flowing oxygen, the temperature was raised to 400° C., kept at this value for 2 days to obtain the final white product, denoted as the zeogrid. The XRD pattern at the intermediate stage (FIG. 1b, black trace) revealed that the repeat distance shrunk from the original 4.0 nm to 3.0 nm. The final sample displayed also a repeat distance of ca. 3.0 mm (FIG. 1c, black trace). In the final product, only the first reflection (100) of the superstructure was clearly observed (FIG. 1c, black trace). Bragg type diffraction of crystalline material at wider angles was not observed.

Figure 2:
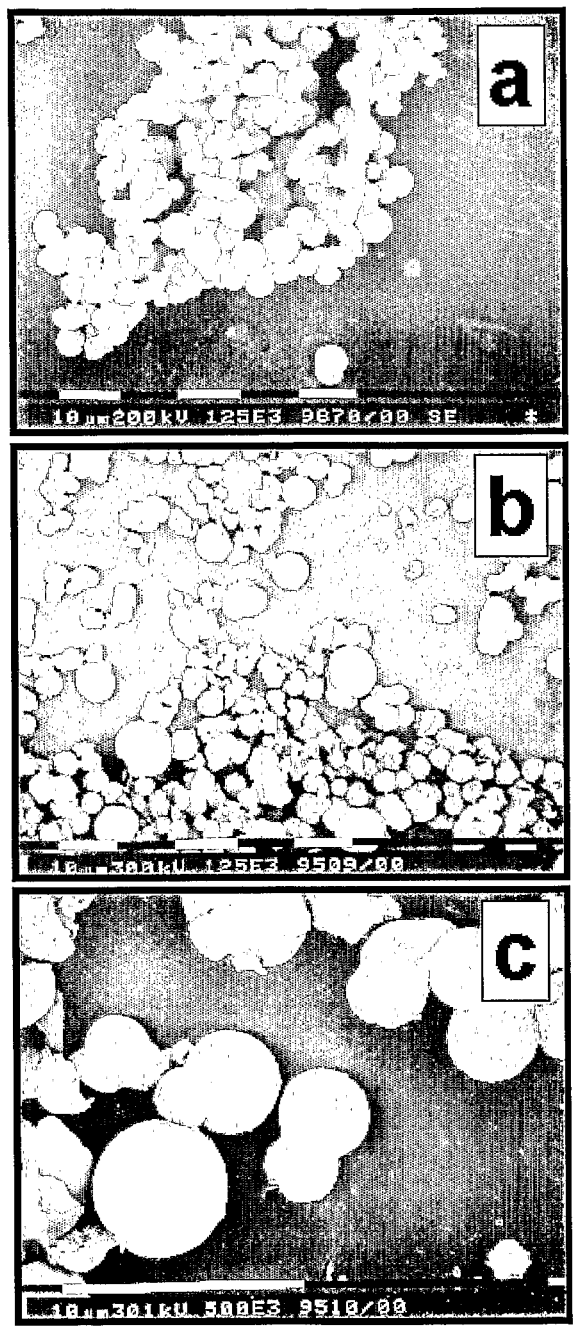
FIG. 2: SEM pictures of zeogrid precipitate, magnification 1,250× (a) and calcined product at magnifications of 1.250× (b) and 5,000× (c).

SEM pictures revealed that the precipitate (FIG. 2a) consisted of spherical particles with diameters from 1 to 6 μm. After calcination (FIG. 2b, c), the particles were reduced in size. Some particles showed fissures; others were disintegrated.

In another preparation, CTMABr was substituted with dodecyltrimethylammonium bromide (DTMABr). The XRD patterns of precipitate and final product again revealed the presence of a layered compound. In the precipitate, the repeat distance obtained with DTMABr was only 3.2 nm compared to 4.0 nm with CTMABr (FIG. 1a, grey trace). The XRD patterns of the intermediate and final product obtained with DTMABr were similar to the ones obtained with CTMABr with a repeat distance of 3.0 μm (FIG. 1b, c, grey traces). The absence of Bragg reflections at higher angles clearly shows that before or during calcination no domains larger than about 15 nm with undisturbed Silicalite-1 structure have been formed.

The original nanoslab suspension was obtained by hydrolysing 37.32 g TEOS (Acros, 98%) in 32.13 g aqueous TPAOH solution (Alfa, 40 wt.-%) under continuous stirring. After the hydrolysis recognized by the homogenization of the two liquids, 30.55 g de-ionized water was added and stirring continued for 24 h.

To an amount of 20 mL of this suspension, a same volume of ethanol (technical grade) was added. Subsequently, 60 mL of a saturated solution of cetyltrimethylammonium bromide (CTMABr, Acros, 99%+) in ethanol was added dropwise under stirring (5 mL/h). A white precipitate formed during CTMABr addition.

In the experiment with DTMABr, a solution of dodecyltrimethylammonium bromide (DTMABr, Acros, 99%) in ethanol (same concentration as the CTMABr experiment) was added. A white precipitate formed overnight.

The precipitates were recovered by filtration over 8 μm pore diameter paper (Whatman 1440 090, grade 40), washed with ethanol on the filter and dried at 60° C. Calcination procedure. The precipitate was compressed into flakes and the flakes crushed and sieved in order to obtain particles with diameters of 0.25-0.5 mm. An amount of 1 g of sample was loaded as a packed bed in a quartz tube and subjected to the calcination program. The heating rate was 0.5° C./min and the gas flow 35 mL/min.

Example 2

Coating of Implantable Devices with a Zeogrid and a Matrix of Silicone Elastomer Preparation Method for Coated Ti-Plates
Materials PDMS-silicone network was synthesised from the following precursors: a siliciumhydride polymer (RTV615B, General Electric Bayer), a siliciumvinyl polymer (RTV615A, General Electric Bayer) and a source of extra hydrides (NM4214). Thin titanium plates were used. The dimensions depended on the experiment-type: 40 mm×20 mm×2 mm for mechanical tests and 15 mm×7 mm×150 μm for in vivo biocompatibility tests.

Alternatively silicone elastomer solutions can be made with DAP® 100% silicone rubber adhesive (from DAP, Inc., Maryland).

Alternatively the adjuvant polymers can be incorporated into the silicone network. Such adjuvant polymerscan for instance be polyethylene glycol (PEG) having a molecular weight preferably of about 2 KDa to 1 MDa and most preferably about 2-500 KDa, copolymers of ethylene oxide and propylene oxide (EO/PO) such as Pluronic® polymers which exhibit surfactant properties, as exemplified below, as well as any other hydrophilic polymers, including, but not limited to, polysaccharides such a hyaluronic acid and chemically modified cellulose, polyamyloses, polydextroses, dextrans, heparins, heparans, chondroitin sulfate, dermatan sulfate, poly (N-isopropylacrylamide), polyurethanes, polyacrylates, polyethyleneimines, polyvinylpyrrolidone, polyvinylalcohol, polyvinylacetate, etc.

For instance the silicone can be dissolved with the adjuvant such as polyethylene glycol of about 2-500 Kda for instance MW 3400 (PEG) in methylene chloride. For instance 20% (w/w) of such PEG.
Surface Pre-Treatment The plates were first acid pickled in a solution containing 40 ml HNO$_3$ (65%) and 2 ml HF (38-40%) for 6 minutes in order to remove the titania oxide layer (Zhao et al., 2001), followed by an ultrasonic treatment in distillated water to remove any acid traces. The plates were then chemically treated with a solution containing 8.8 M H$_2$O$_2$ and 0.1 M HCl at 80° C. for 1 hour to obtain a cracked titania gel layer (Wang et al., 2002). Just before coating the plates were dried with an Argon flux.
Synthesis Coating Mixture 0.2 g zeogrid were suspended in 0.5 g MIBK (methyl isobutyl ketone). The suspension was homogenised for 10 minutes to obtain finally suspended zeogrid particles. 0.2 g hydrides (NM) were added. This mixture was stirred for 5 minutes in order to bind the zeogrid to the silicone according to the following reaction:

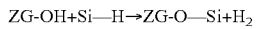

ZG-OH+Si—H→ZG-O—Si+H$_2$

Gas and heat formation confirms the reaction. In the last step 0.1 g extra hydrides (RTV615B) and 1 g vinyls (RTV615A) were added. This mixture was stirred for 20 seconds.

To obtain a silicone mixture without zeogrid the same procedure was followed, except that no zeogrid was added to the synthesis mixture.
Coating Procedure A spincoater was used to create a thin homogeneous coating.

The pre-treated plates were wetted with a thick zeogrid-silicone mixture layer (or just a silicone layer) to cover the whole surface. This layer was spincoated on the plates at 400 to 1300 rpm. A thin homogeneous layer was obtained. The thickness depended on the rotational speed. At 1300 rpm the thickness was about 50 μm (Villani, 2002). For mechanical experiments the adopted rotational speed was 400 rpm. For biocompatibility experiments the adopted speed was 1000 rpm. To cure the silicone network the plates were heated at a rate of 1° C. per minute to 140° C. This temperature was maintained for approximately 12 hours.

Attachment of Silicone on Ti

Two different treatments of the surface of Ti plates have been tested. The first treatment comprises a treatment with HF and a second treatment comprises a treatment with $HNO_3$.

The distinction between "single" and "double" comes for from the different test samples which are made for the joining (attachment) tests. At a "single" sample on one plate silicon layer is introduced and with epoxy glue one attaches a second plate for the tearing test. At "double" samples two Ti-plates are directly joined by silicone. There no more adhesive used for this "double" samples. A blanco Ti-plates glued to each others with epoxy adhesive is used as reference. This way also the attachment strength of the adhesive to Ti is known.

Testing the Attachment

Figure 5:
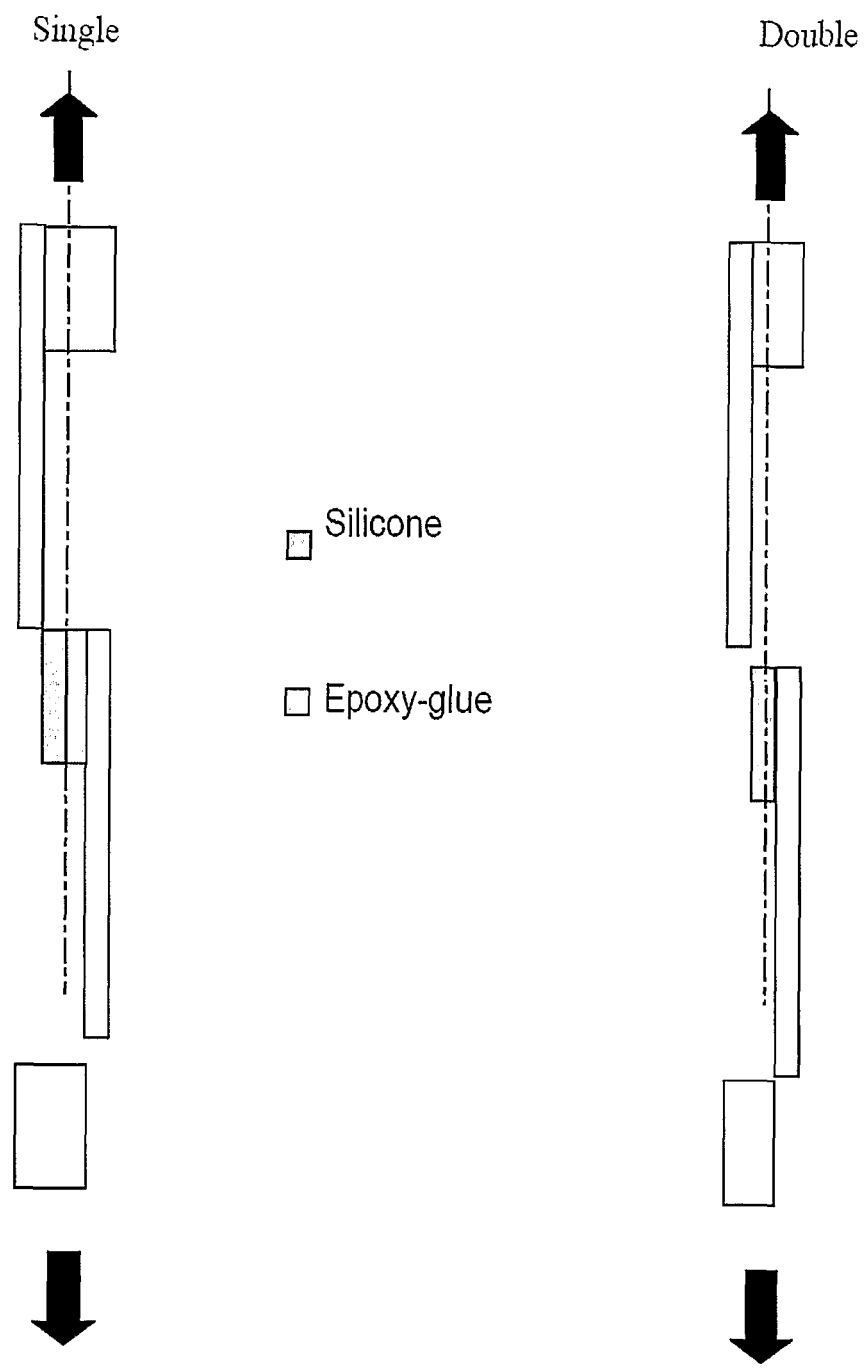
FIG. 5: System for testing the attachment

The system for testing the attachment is shown in FIG. 5.

Results

Figure 6:
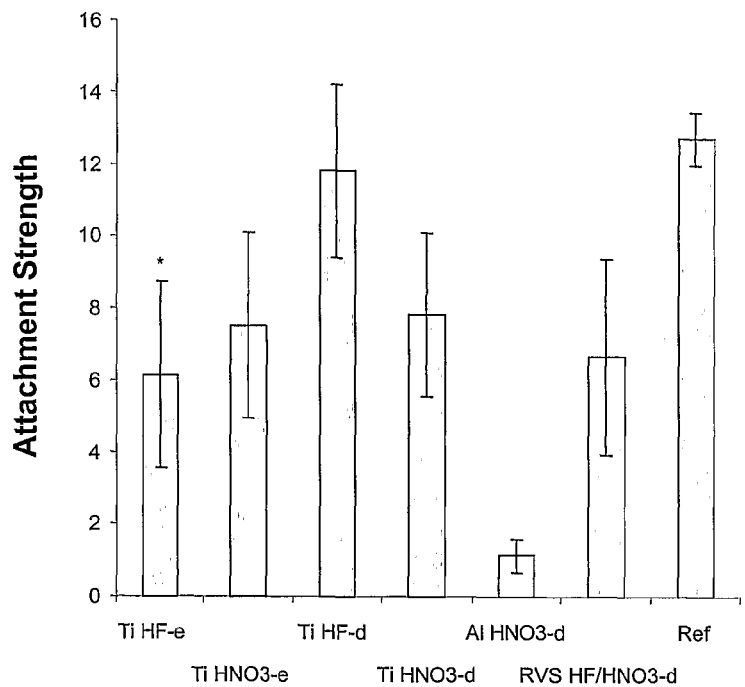
FIG. 6: Graphic overview of the attachment strength of silicon coating at Ti, RVS and Al depending on the pretreatment of the surface of the substrate.

From the tension-replacement curve (FIG. 7) the maximal tear tension was calculated, using the Von Mises criterium. This is considered a validated value for the strength of attachment. The results are demonstrated in Table 1 and FIG. 6.

TABLE 1

Overview of the strength of attachment of silicone at Ti, RVS and Al depending on the surface treatment of the substrate.

| Material | Treatment | Attachment strength (MPa) |
| --- | --- | --- |
| Ti | HF-single | >6.14 ± 2.62* |
| Ti | $HNO_3$-single | 7.52 ± 2.59 |
| Ti | HF-double | 11.81 ± 2.39 |
| Ti | $HNO_3$-double | 7.83 ± 2.26 |
| Al | $HNO_3$-double | 1.12 ± 0.47 |
| RVS | HF/$HNO_3$-double | 6.67 ± 2.75 |
| Ref | Epoxy-glue | 12.73 ± 0.74 |

Figure 7:
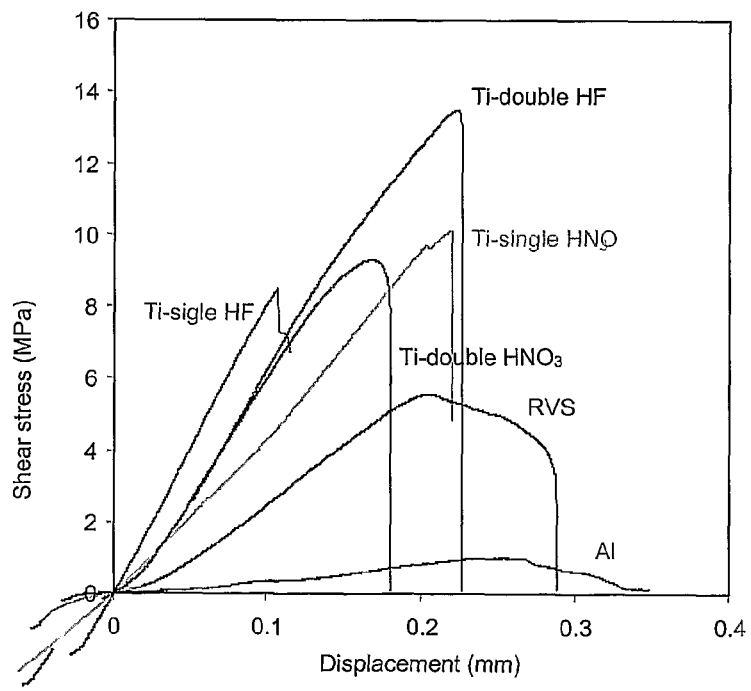
FIG. 7: Typical tension replacement curve of Ti, RVS and Al with a silicon coating.
Figure 8:
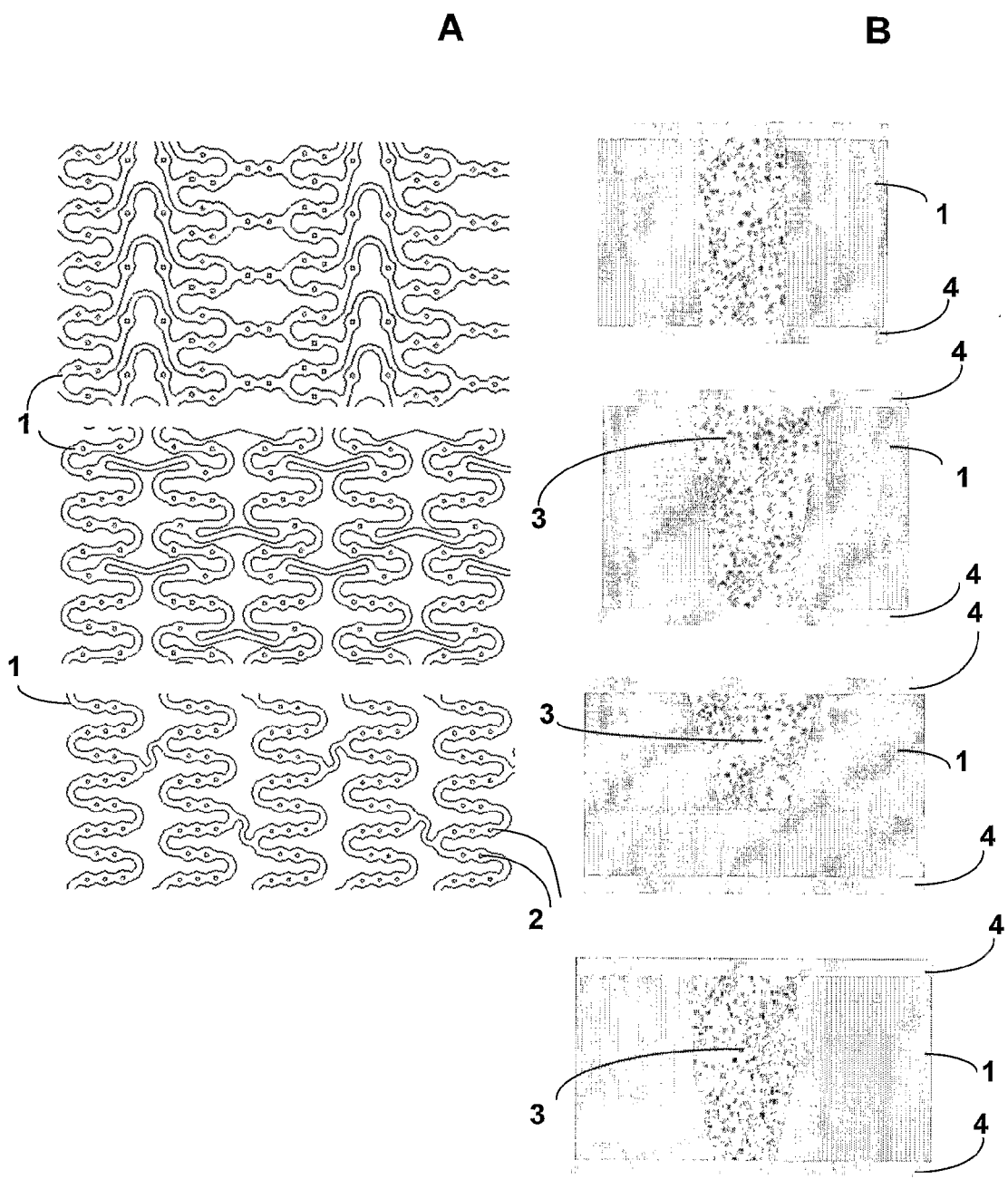
FIG. 8: (A) Top plan view on tubular prosthesis that has been cut in its longitudinal direction and pressed into a flat screen, the screen showing the holes (reservoirs) in the outer surfaces of the prosthesis. (B) Illustration on a larger scale and in a cross sectional view of the holes in the strut. The holes are filled by a matrix comprising zeogrid particles; (1) substrate (for instance the struts of an expandable stent), (2) holes (reservoirs) in the substrate (in various shapes perforating or non-perforating as an illustration of different embodiments), (3) a matrix comprising zeogrid particles filling the holes, (4) an optional coating on the surface of the substrate and sealing the holes
Figure 9:
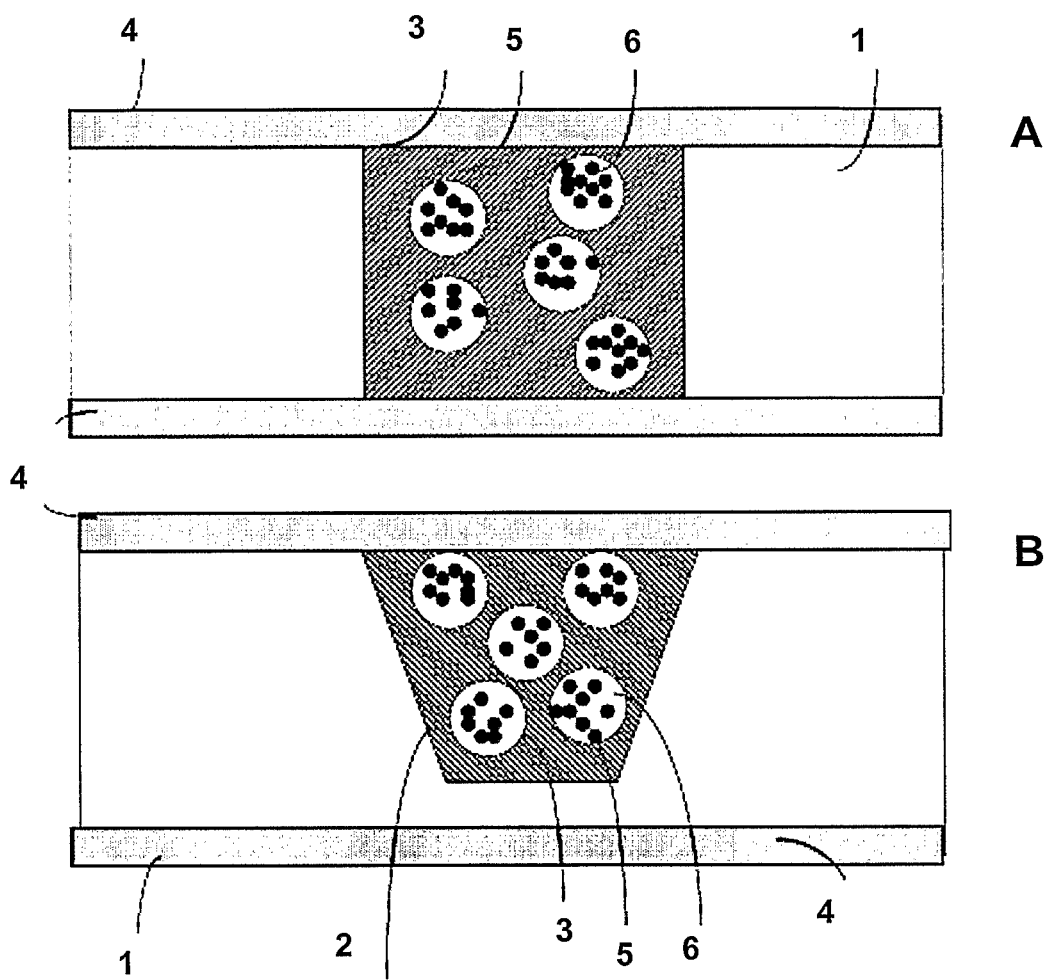
FIG. 9: Display of a substrate (for instance the struts of a expandable stent) (1), holes (reservoirs) in the substrate (in various shapes perforating or non perforating as an illustration of different embodiments) (2), a matrix comprising grid particles filling the holes (3), an optional coating on the surface of the substrate and sealing the holes (4) and zeogrid (5) comprising drug (6).

The results are demonstrated in FIG. 7 as a typical tension replacement curve of Ti, RVS and Al with a silicone coating. The treatment of Ti with HF ensures a better joining between the substrate and the silicone coating. This is shown by both the results of only glued and the twice glued samples. At the only glued samples it is each time the adhesive which breaks down and never the silicon-Ti interface. This means that the attachment strength amount to at least 6.2 MPa. In the group of substrates with HNO3 treated surfaces there are samples on which the silicone-Ti interface breaks down. This is an indirect indication that HF-treatment realises a more stable interface. More direct indications come of the twice-glued samples, where always the silicon-Ti interface broke down. HF-treated samples had an attachment strength of 11.8 MPa and HNO3 treated samples only an attachment strength of 7.83 MPa. Both the HF and the HNO3 treatments had more impact on the joining of Ti and silicon than the other metal (Al and RVS). The attachment strength of silicon joined on Ti was significantly higher than Al and RVS.

Example 3

β-Estradiol Release from Zeogrid

Loading of the zeogrid sample with β-estradiol proceeds as follows. 50 mg β-estradiol is dissolved in 100 ml methylenechloride. 500 mg of zeogrid is suspended in the solution. Everything is stirred during 24 hours in a closed container. After 24 hours, the container is opened and the methylenechloride is evaporated at room temperature. The resulting powder is further dried and kept during 24 hours under reduced pressure to remove the solvent.

Release of β-estradiol from zeogrids. Simulated body fluid (SBF) was used as dissolution medium. SBF was prepared by first dissolving 1% SLS (Sodium lauryl sulphate) and 0.90% NaCl in distilled water. The solution was mixed with ethanol in a volume ratio solution:ethanol of 24:1.

The in-vitro release experiments were carried out at room temperature by dispersing 10 mg quantities of the loaded zeogrid into 20 ml quantities of SBF. In order to avoid limitations of the delivery rate by external diffusion constraints, continuous stirring is maintained. The release profile was obtained by measuring drug concentration in the fluid after different times by means of HPLC.

Figure 3:
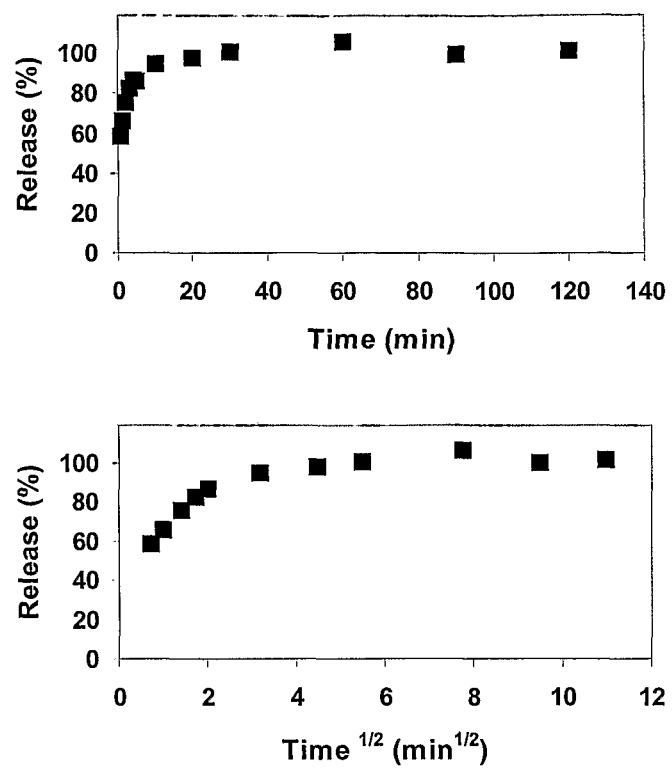
FIG. 3: β-Estradiol release from zeogrid against time (a) and against square root of time (b).

FIG. 3a shows the percentage of β-estradiol release from the zeogrid sample against time. The release of β-estradiol from zeogrid is completed after 30 minutes. β-estradiol release against square root of time is presented in FIG. 3b. The linear relation between concentration of β-estradiol in solution and square root of time reveals that the drug release if governed by diffusion through the pores of the zeogrid.

Figure 4:
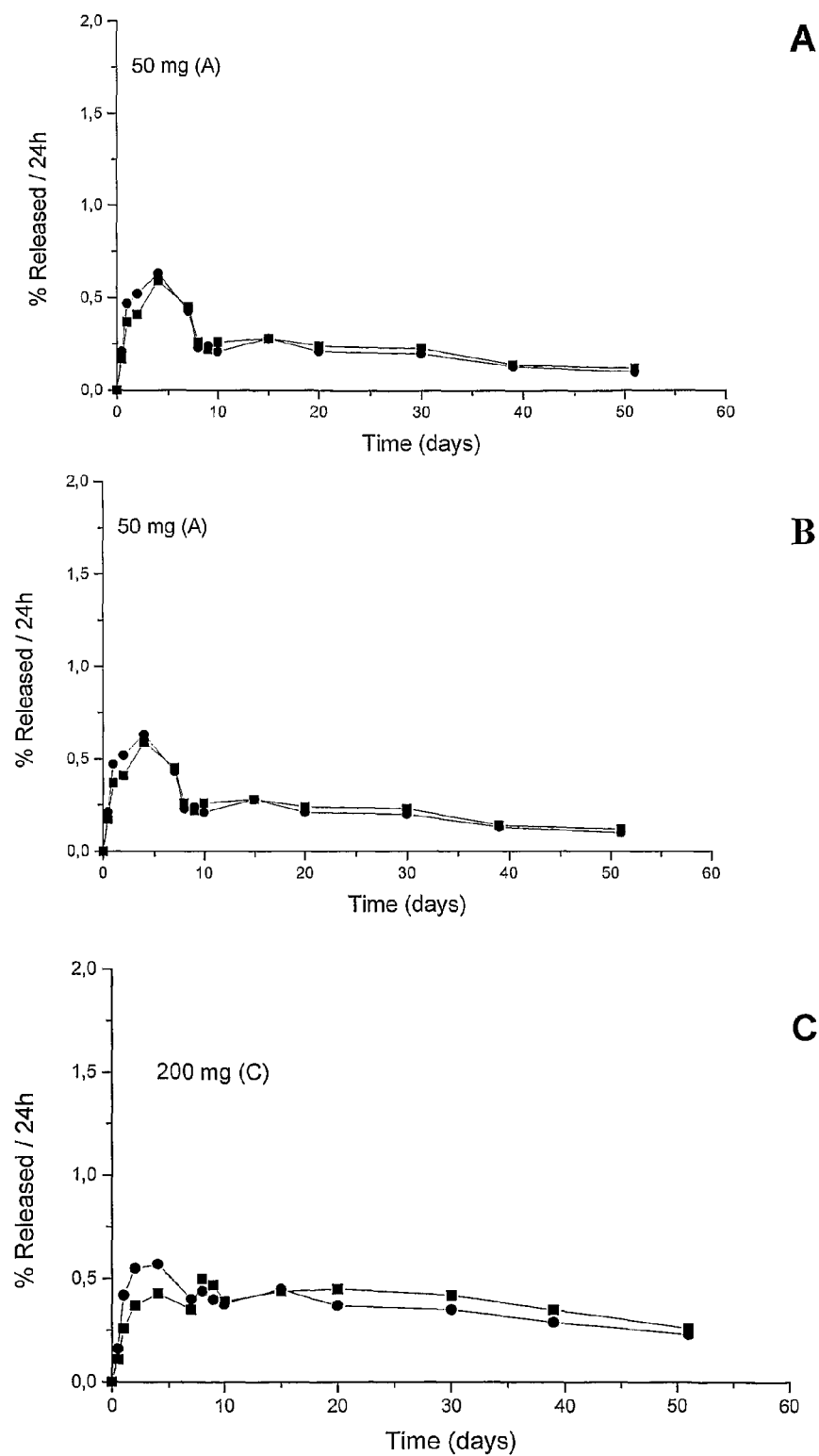
FIG. 4: β-Estradiol release from zeogrid in a silicone coating. Three drug doses are tested: 2.3 mg (a), 4.5 mg (b) and 9.1 mg (c)

Slower release of the β-estradiol can be obtained by dispersing the drug-loaded zeogrids in a coating, f.i. a silicone coating:

Metal plates are coated with silicone/zeogrid loaded with β-estradiol and put in the release medium. Every day, the release medium is replaced and is analysed with HPLC to determine the concentration of β-estradiol. The test is performed in double. Three drug densities are tested: Plate A (2.3 mg drug), Plate B (4.5 mg drug), plate C (9.1 mg drug). Drug-release curves are shown in FIG. 4 (a, b, c).

Example 4

Coating of a Stent with a Cis-Hydrogenated Fatty Acid (CHFA) Based Coating that Contains Zeogrids The method to producing CHFA-based coating is described in WO 98/65275. Following steps are required to coat a medical device with a CHFA-coating that contains drug-loaded zeogrids:

a) Cleaning, degreasing and drying of the prosthesis
b) Dipping of the prosthesis in a deoxidative solution and air drying it. Eventually, this step can be omitted.
c) Loading the zeogrids with the required therapeutic agent.
d) Mixing of drug-loaded zeogrids into the CHFA-based coating. This is preferably performed after the last step of the production of the CHFA, when the CHFA is still in the liquid phase.
e) Making an emulsion or solution of the soya oil-based cis-hydrogenated fatty acid based coating that contains drug-loaded zeogrids and a solvent, preferably in a liquid state of the cis-hydrogenated fatty acid based coating.
f) In this emulsion/solution, one or more therapeutic agents can be dissolved when the CHFA-based coating did not yet contain a therapeutic agent or one or more additional therapeutic agents may be dissolved when the CHFA already contained one or more therapeutic agents. The therapeutic substance needs only to be dispersed throughout the solvent/CHFA emulsion or solution so that it may be either in a true solution with the solvent/CHFA emulsion or solution or dispersed in fine particles in the solvent/CHFA emulsion or solution.

g) Stirring of the obtained solution until achievement of a homogeneous mixture/solution h) Applying to the prosthesis body of the therapeutic agent containing solvent/CHFA emulsion or solution using dip coating or spray coating or any other coating method.

i) Air-dry until the solvent is evaporated.

j) Optionally, the previous steps are repeated multiple times, eventually using different therapeutic agents.

k) Further air-dry the prosthesis (in a sterile, laminar flow).

After drying, a topcoat can be applied by using dip coating, spray coating or any other coating method.

After drying, the obtained coated prosthesis can be used as such or further dried and sterilized. Light-protection is advisable to maintain the biocompatible characteristics when stored.

Example 5

Pre-Clinical Evaluation of Coronary Stent Dipcoated with a Cis-Hydrogenated Fatty Acid Based Coating (Ciscoat) and of the Cis-Hydrogenated Fatty Acid Loaded with a Molecular Sieve (Zeogrids)

Materials and Methods
Porcine Coronary Model

Domestic crossbred pigs of both sexes weighing 20-25 kg were used. They were fed with a standard natural grain diet without lipid or cholesterol supplementation throughout the study. All animals were treated and cared for in accordance with Belgium National Institute of Health Guide for care and use of laboratory animals.

The pigs were sedated with azaperone 0.1 ml/kg (Stresnil®, Janssen Pharmaceutics, Beerse, Belgium) and anesthetized with intravenous ketamine (Ketalar®, Parke Davis, Morris Plains, N.J., Warner Lambert, Belgium, 5 mg/kg) for induction and a mixture of ketamine at a rate of 0.1 mg/kg/hr and 10 mg/ml Propofol (Diprivan® 1%, NV AstraZeneca SA, Belgium) at a rate of 2 mg/kg/hr for maintenance intravenously. Adequate anesthesia was determined by the loss of the limb withdrawal reflex. The pigs were intubated in 6 F tracheal tubes and ventilation (Mark 7A®, Bird Cooperation®, Palm Springs, Calif.) was started using a mixture of 20 vol. % of pure oxygen and 80 vol. % of room air. Continuous electrocardiography and pressure were performed throughout the procedure. An external carotid artery was surgically exposed and an 8 Fr. intra-arterial sheath was introduced over a 0.035" guide wire. Heparin 10000. IU and 900 mg lysin acetylsalicylas (Aspegic®), Sanofi-synthelabo S.A.N.V., Brussel, Belgium) were administered intravenously as a bolus. The coronary artery was visualized using an 8 Fr. Judkins L 3.0 catheter and Hexabrix was used as contrast agent. The stents were mounted on a conventional coronary angioplasty balloon catheter and then deployed in a selected arterial segment using an inflation pressure of 8 atm. for 30 seconds. Coronary angiography, after intra-arterial administration of nitroglycerine (0.25 mg), was performed to confirm vessel patency after stent implantation. Finally, the carotid arteriotomy was repaired and the dermal layers were closed using standard technique. The pigs were sacrificed by using an intravenous bolus of 20 ml oversaturated potassium chloride. For these follow-up studies, the instrumentation of the pigs was identical to those used during the implantation procedure.

Stent Implantation

In the first study bare stents, coating A (5 min hydrogenation time) and coating B (30 min hydrogenation time) stents (each group, n=2) were implanted in the coronary arteries of 2 pigs and followed for 5 days to evaluate inflammatory response and thrombus formation. Furthermore bare stents (n=2), coating A (n=5) and coating B (n=4) stents were implanted randomly in the coronary arteries of pigs. Pigs were sacrificed after 4 weeks to evaluate peri-strut inflammation and neointimal hyperplasia.

In the second study Ciscoat C was used (15 min hydrogenation time) as Ciscoat. Ciscoat mixed with 5% wt % Zeogrids (Ziscoat 5%, n=6), mixed with 10% wt % Zeogrids (Ziscoat 10%, n=7) and Ciscoat C coated (Ciscoat, n=6) stents were implanted in the coronary arteries of 6 pigs. Pigs were sacrificed after 4 weeks to evaluate peri-strut inflammation and neointimal hyperplasia.

Stent implantation in the right coronary artery or/and left anterior descending and the circumflex coronary artery was performed randomly. The guiding catheter was used as a reference to obtain an oversizing from 10 to 30%.

Measurements
Histopathology

At follow-up, the stented artery segment will be carefully dissected together with an 1 cm minimum vessel segment both proximal and distal to the stent after pressure fixation using a 10% formalin solution at 80 mmHg. The segment will be fixated in a 5% formalin solution. The sections will be embedded in plastic (Technovit). Sections from each arterial segment will be stained with hematoxylin-eosin, elastica von Gieson, PTAH and Mason's trichrome stain. Light microscopic examination was performed by an experienced pathologist who was blinded to the type of stent used. Injury of the arterial wall due to stent deployment (and eventually inflammation induced by the polymer) was evaluated for each stent filament and graded as described.

Grade 0=internal elastic membrane intact;

Grade 1=internal elastic membrane lacerated, media compressed but not lacerated;

Grade 2=media visibly lacerated, external elastic membrane compressed but intact;

Grade 3=external elastic membrane lacerated or stent filament residing in the adventitia.

Inflammatory reaction at each stent filament was carefully examined, searching for inflammatory cells, and scored as followed:

1=sparsely located histolymphocytes surrounding the stent filament;

2=more densely located histolymphocytes covering the stent filament, but no lymphogranuloma and/or giant cells formation found;

3=diffusely located histolymphocytes, lymphogranuloma and/or giant cells, also invading the media.

Mean score=sum of score for each filament/number of filaments present.

Morphometry

Morphometric analysis of the coronary segments harvested was performed using a computerized morphometry program (Leitz CBA 8000). Measurements of lumen area, lumen area inside the internal elastic lamina, and lumen inside the external elastic lamina were performed. Furthermore, area stenosis and neointimal hyperplasia area were calculated.

The ratio of balloon area/internal elastic lamina area (Bal-a/IEL-a) was applied to provide the normalized value of oversizing related to the extent of mechanic arterial injury during stent implantation.

Statistics

Data are presented as mean values ±SD, n represents the number of stents. The histological and morphometric values of each stent are calculated, and the linear regression of arterial injury with neointimal hyperplasia for bare stents and for the mean values of coating A and B, for Ciscoat coated and for the mean values of Ziscoat 5% and Ziscoat 10% are performed. As the number of stents in the first study is limited, no statistic comparison is performed among the groups. In the second study one-way analysis of variance (ANOVA) followed by Dunnett's post-hoc was used for comparison. A p value<0.05 is considered as statistically significant.

A. First Study—Aims
1. Evaluation of early inflammatory response and thrombus formation of Ciscoat coated stents (coating A (5 min hydrogenation time) and coating B (30 min hydrogenation time) in a porcine coronary artery at 5 days
2. Evaluation of in-stent neointimal hyperplasia of Ciscoat-coated stents at 4 weeks in a porcine coronary model
3. Comparison of non-coated stents with coating A and coating B stents Results All stents were implanted successfully. No dissection noted by coronary angiography and other complications were observed. All pigs were sacrificed at the study end points.

Histopathology

In the first study, stent struts mild to moderate compressed internal elastic lamina and media were observed at 5 days. Medial layer lacerated was noted at one section of coating A stent. Arterial injury was low and comparable among the three groups (bare: 0.28±0.14, coating A: 0.30±0.16, coating B: 0.26±0.14). Stent struts were covered by a thin thrombotic meshwork. The thrombus formation of coating A and B stents was slightly higher than the bare stents (bare: 1.00±0.00, coating A: 1.06±0.07, coating B: 1.12±0.07). Inflammatory cells were adhesive to the injury site and infiltrated into the thrombotic meshwork. Peri-strut inflammation (bare: 1.00±0.00, coating A: 1.02±0.04, coating B: 1.00±0.00) was comparable among the groups.

At 4 weeks follow-up (Table 2), the neointima of the bare, coating A and B stent groups consisted of smooth muscle cells within an extracellular matrix. Increased arterial injury was observed in coating A and B groups (bare: 0.27±0.14, coating A: 0.41±0.23, coating B: 0.55±0.48). Lacerated medial layer was found at one stent section of both coating A and B groups. Especially in one coating B stent (CISCOAT-5, LAD), lacerated external elastic lamina was observed. Inflammatory cells were present around the stent struts and neointima. The peri-strut inflammatory response of the coating A stents (1.00±0.00) was unique and low. Increased peri-strut inflammatory response was found in the coating B stent (CISCOAT-5, LAD). A few stent struts showed increased peri-strut inflammation scored as 3, which resulted in an increased inflammatory score of coating B stent group (bare: 1.08±0.29, coating A: 1.00±0.00, coating B: 1.24±0.44) and arterial injury.

Morphometry

In the first study (Table 2), the lumen area of coating A (5.58±2.12 mm$^2$) and coating B (5.11±1.88 mm$^2$) stent groups was slightly lower than the bare stent group (5.95±1.69 mm$^2$) at 4 weeks. Neointimal hyperplasia (bare: 1.46±0.28, coating A: 1.57±0.62, coating B: 1.64±1.16) and area stenosis of coating A and coating B were comparable to the bare stent group, although the oversizing (Balloon-a/IEL-a) of the coating A and coating B stents was higher than the bare stents.

B. Second Study—Aims
1. Evaluation of the biocompatibility of Ciscoat C (15 min hydrogenation time) loaded with 5% and 10% Zeogrids (Ziscoat) coated stents in a porcine coronary model
2. Comparison of Ciscoat C loaded with 5% and 10% Zeogrids (Ziscoat) coated stents with Ciscoat C coated stents Results In the second study (Table 3), the arterial injury of stent implantation was low (Ciscoat 0.31±0.15, Ziscoat 5%: 0.41±0.26, Ziscoat 10%: 0.31±0.21). Lacerated internal elastic lamina was observed in all sections. Some stent struts showed lacerated medial layer. In one Ziscoat 5% coated stent (Ziscoat-7, LCX), lacerated external lamina was found in a few stent struts. Meanwhile increased peri-strut inflammation was observed in all proximal, middle and distal sections of this stents. Limited and unique peri-strut inflammation however was noted in all other stents (Ciscoat: 1.00±0.00, Ziscoat 5%: 1.12±0.27, Ziscoat 10%: 1.00±0.00).

Morphometry

In the second study (Table 3), the lumen area of Ziscoat 10% coated stents was larger than the Ciscoat and Ziscoat 5% coated stents (Ciscoat: 4.74±1.60, Ziscoat 5%: 4.32±1.65, Ziscoat 10%: 5.13±1.59). Furthermore the neointimal hyperplasia of Ziscoat 10% coated stents was slightly lower then the other two groups. The neointimal hyperplasia of Ziscoat 5% coated stent (Ziscoat-7, LCX) was the highest (2.07 mm$^2$), which was responsible to the increased neointimal hyperplasia of Ziscoat 5% coated group (Ciscoat: 1.27±0.60, Ziscoat 5%: 1.42±0.63, Ziscoat 10%: 1.09±0.42). Compared to the Ciscoat coated group, no differences of lumen area, neointimal hyperplasia, area stenosis were observed among the groups (P>0.05).

Figure 10:
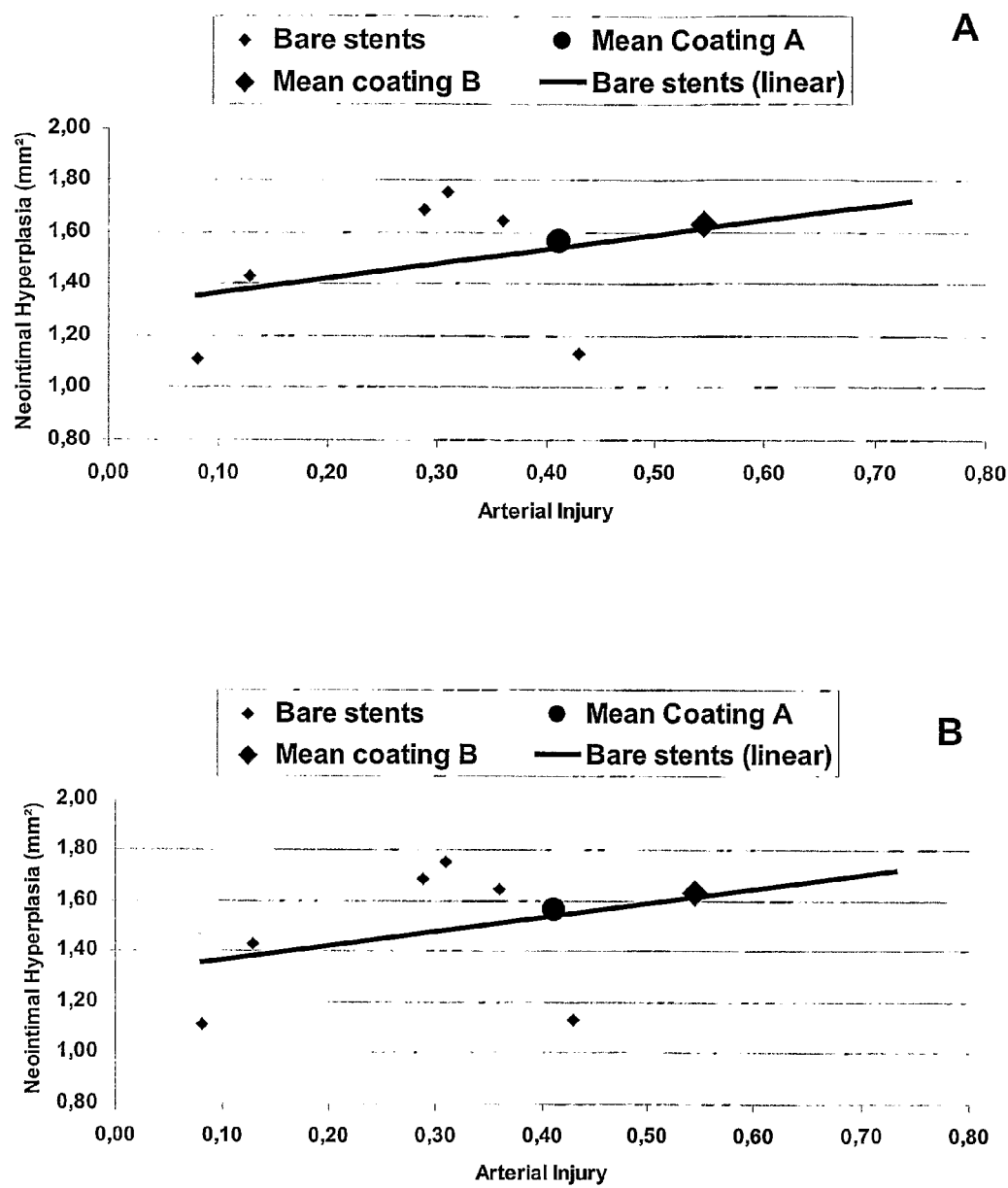
FIG. 10: Linear regression analysis of (A) the correlation between arterial injury and neointimal hyperplasia for bare stents, coating A and coating B; and (B) the correlation between arterial injury and neointimal hyperplasia for Ziscoat 5% and Ziscoat 10% coated stents

By linear regression of arterial injury with neointimal hyperplasia, the mean values of neointimal hyperplasia for both coating A and coating B are on the linear approximation of the bare stents (FIG. 10, A). Furthermore the mean values of neointimal hyperplasia for Ziscoat 5% and Ziscoat 10% coated stents are on the linear approximation of the Ciscoat coated stents (FIG. 10, B).

Conclusions

At 5 days, the coating A and B stents induced a similar histopathological response and thrombus formation compared to the bare stents.

At 4 weeks follow-up, one coating B and one Ziscoat 5% coated stent induced severe peri-strut inflammation, resulting in an increased arterial injury and neointimal hyperplasia, probably due to contamination of the stent.

At 4 weeks, the peri-strut inflammation, neointimal hyperplasia and area stenosis of coating A and B stents were comparable to the bare stents. The Ziscoat 5% and Ziscoat 10% coated stents were comparable to the Ciscoat coated stents.

Interestingly, it was found that the area stenosis was significantly lower for the Ziscoat 10% compared to the stents coated with Ciscoat alone. Thus, the zeogrids appear to have an anti-restenotic effect.

Using linear regression analysis comparing arterial injury with neointimal hyperplasia, the mean values of neointimal hyperplasia for both A and B are on the linear approximation of the bare stents. The mean values of neointimal hyperplasia for Ziscoat 5% and Ziscoat 10% coated stents are on the linear approximation of the Ciscoat coated stents.

Both 5 days and 4 weeks data showed that the function of coating A and B stents was similar to the bare stents. Both coating A and B did not induce increased inflammation and proliferative tissue response.

Adding 5% and 10% Zeogrids to Ciscoat coating did not influence the function of the coating material and show a good biocompatibility to the coronary arterial wall.

It can be concluded from these studies that both Ciscoat and Ziscoat are biocompatible coatings.

TABLE 2

Histomorphometric analysis of Ciscoat stented vessel segments
4 weeks follow-up in porcine coronary arteries

|  | n | LA (mm$^2$) | NIH(mm$^2$) | AS(%) | Bal-a/IEL-a | Inflammation | Injury |
|---|---|---|---|---|---|---|---|
| Bare | 2 | 5.95 ± 1.69 | 1.46 ± 0.28 | 21 ± 7 | 1.14 ± 0.09 | 1.08 ± 0.29 | 0.27 ± 0.14 |
| Coating A | 5 | 5.58 ± 2.12 | 1.57 ± 0.62 | 24 ± 12 | 1.24 ± 0.16 | 1.00 ± 0.00 | 0.41 ± 0.23 |
| Coating B | 4 | 5.11 ± 1.88 | 1.64 ± 1.16 | 26 ± 21 | 1.25 ± 0.19 | 1.24 ± 0.44 | 0.55 ± 0.48 |

LA = lumen area; NIH = neointimal hyperplasia,; AS = area stenosis; IEL = internal elastic lamina; Bal-a/IEL-a = balloon-area/IEL-area.

TABLE 3

Histomorphometric analysis of Ziscoat stented vessel segments
4 weeks follow-up in porcine coronary arteries

|  | n | LA (mm$^2$) | NIH(mm$^2$) | AS(%) | Bal-a/IEL-a | Inflammation | Injury |
|---|---|---|---|---|---|---|---|
| CISCOAT | 6 | 4.74 ± 1.60 | 1.27 ± 0.60 | 23 ± 13 | 1.43 ± 0.22 | 1.00 ± 0.00 | 0.31 ± 0.15 |
| ZISCOAT 5% | 6 | 4.32 ± 1.65 | 1.42 ± 0.63 | 27 ± 16 | 1.47 ± 0.17 | 1.12 ± 0.27 | 0.41 ± 0.36 |
| ZISCOAT 10% | 7 | 5.13 ± 1.59 | 1.09 ± 0.42 | 18 ± 8 | 1.35 ± 0.23 | 1.00 ± 0.00 | 0.31 ± 0.21 |

One-way analysis of variance (ANOVA) followed by Dunnett's post-hoc was used for comparison. The p values of all items were >0.05.
LA = lumen area; NIH = neointimal hyperplasia,; AS = area stenosis; IEL = internal elastic lamina; Bal-a/IEL-a = balloon-area/IEL-area.

Example 6

In Vitro Release of Methylprednisolone (MP) and Methylprednisolone Sodium Succinate (MPS) from a Cis-Hydrogenated Fatty Acid Based Coating (Ciscoat) and from a Molecular Sieve (Zeogrid) Optionally Comprised in a Cis-Hydrogenated Fatty Acid Based Coating Methylprednisolone (MP) and Methylprednisolone succinate (MPS) (J Pharm Sci. 1987 July; 76(7):528-34. Toutain P L, et al.) are corticosteroids. Methylprednisolone is a hormone naturally produced by the adrenal glands which have many important functions, including control of inflammatory responses. Methylprednisolone sodium succinate is a synthetic corticosteroid of the natural variant. It has the same metabolic and anti-inflammatory actions as the parent compound, methylprednisolone; but is a water-soluble ester salt.
Materials and Methods
The Experimental Groups:
1. (Ciscoat loaded with MP)
2. Ciscoat+(zeogrids loaded with MP=drug-containing substrate or DCS))
3. (Ciscoat loaded with MP)+(zeogrids loaded with MP)
4. (zeogrids (loaded with MP) without Ciscoat
5. (Ciscoat loaded with MPS)
6. Ciscoat+(zeogrids loaded with MPS)
7. (Ciscoat loaded with MPS)+(zeogrids loaded with MPS)
8. (zeogrids loaded with MPS) without Ciscoat
9. Ciscoat+(zeogrids loaded with MP)+(zeogrids loaded with MPS)

Preparation of the Drug Loaded Coatings

Zeogrid were loaded as follows: MP or MPS was solved in a solvent (dimethylether). The Zeogrids were impregnated with the solvent comprising the MP or the MPS. Consequently the solvent was evaporated. By this method the zeogrids were loaded with MP or MPS for 20% of the weight (1 mg loaded zeogrid contains about 200 µg of MP or MPS).

The cis-hydrogenated omega-3 fatty acid based coating (Ciscoat) was prepared from soy oil according to the hydrogenation process described in WO 98/54275 designed to significantly eliminate the formation trans-unsaturated fatty acid compounds.

The metal carrier for the coating was a stainless steel plate with a total surface of 1 cm$^2$ (front surface, back surface and surface of the edge). The samples 4 and 8 contain only zeogrid loaded with respectively MP and MPS, but no Ciscoat and metal carrier.

Every sample comprised about 200 µg MS or MPS. The loaded dose was controlled as follows: the metal carriers were dipped in melted Ciscoat at a temperature of 80° C., and weighed. A sample can carry 4.9 mg Ciscoat. Thus 4.9 mg Ciscoat had to be arranged to comprise about 200 µg of MS or MPS.

Ciscoat was divided over small vials of precisely know weight (1.4 ml Ciscoat/vial). The filled vials were weighed again to determine the mass of Ciscoat. The masses are displayed hereunder in Table 4.

TABLE 4

| Vial nr. | Mass empty | Mass filled | Mass fat |
|---|---|---|---|
| 1 | 2.83963 | 4.05376 | 1.21413 |
| 2 | 2.84275 | 3.91444 | 1.07169 |
| 3 | 2.86723 | 3.94664 | 1.07941 |
| 4 |  |  |  |
| 5 | 2.84678 | 4.07397 | 1.22719 |
| 6 | 2.83381 | 3.89863 | 1.06482 |
| 7 | 2.88289 | 4.03484 | 1.15195 |
| 8 |  |  |  |
| 9 | 2.82885 | 3.88634 | 1.05749 |

Weights in g

Knowing that 4.9 mg ciscoat had to comprise about 200 µg MP or MPS a correct amount of zeogrid (ZS) loaded with MP or MPS had to be added to the ciscoat (see hereunder in Table 5).

TABLE 5

| Vial nr. | mass MP theor. | mass MP real | mass MP ZG theor. | mass MP ZG real | mass MPS theor. | mass MPS real | mass MPS theor ZG | mass MPS real ZG |
|---|---|---|---|---|---|---|---|---|
| 1 | 49.556 | 49.58 | — | — | — | — | — | — |
| 2 | — | — | 218.712 | 218.8 | — | — | — | — |
| 3 | 22.028 | 21.97 | 110.145 | 110.15 | — | — | — | — |
| 4 | — | — | 1 | 1.01 | — | — | — | — |
|   | — | — |   | 1.05 | — | — | — | — |
|   | — | — |   | 1.03 | — | — | — | — |
| 5 | — | — | — | — | 50.089 | 50.16 | — | — |
| 6 | — | — | — | — | — | — | 217.31 | 217.22 |
| 7 | — | — | — | — | 23.509 | 23.55 | 117.546 | 117.77 |
| 8 | — | — | — | — | — | — | 1 | 1.02 |
|   | — | — | — | — | — | — |   | 1.08 |
|   | — | — | — | — | — | — |   | 1.03 |
| 9 | — | — | 107.907 | 107.74 | — | — | 107.907 | 107.86 |

Weights in mg

Since a homogenous solution was not obtained at the preparation of vial 6 a new vial was prepared with half the dose of MPS (Vial 6B is), see table 6 hereunder:

TABLE 6

| Vial nr. | mass MP theor. | mass MP real | mass MP ZG theor. | mass MP ZG real | mass MPS theor. | mass MPS real | mass MPS theor ZG | mass MPS real ZG |
|---|---|---|---|---|---|---|---|---|
| 6 bis |  |  |  |  |  |  | 118.405 | 118.51 |

Weights in mg

The test samples were dipped in the melted Ciscoat at 80° C. comprising MP or MPS (in triplicate per condition). After solidification of the Ciscoat the samples were put in 10 ml volume test vials. For the samples no. 4 and 8 an amount of MP or MPS loaded zeogrids adjusted to obtain the same drug load were added to the test tube (in triplicate per condition). Except the sample no. 6, which comprised a drug load of about 100 µg, all other samples comprised about 200 µg of MP or MPS.

Results

Figure 11:
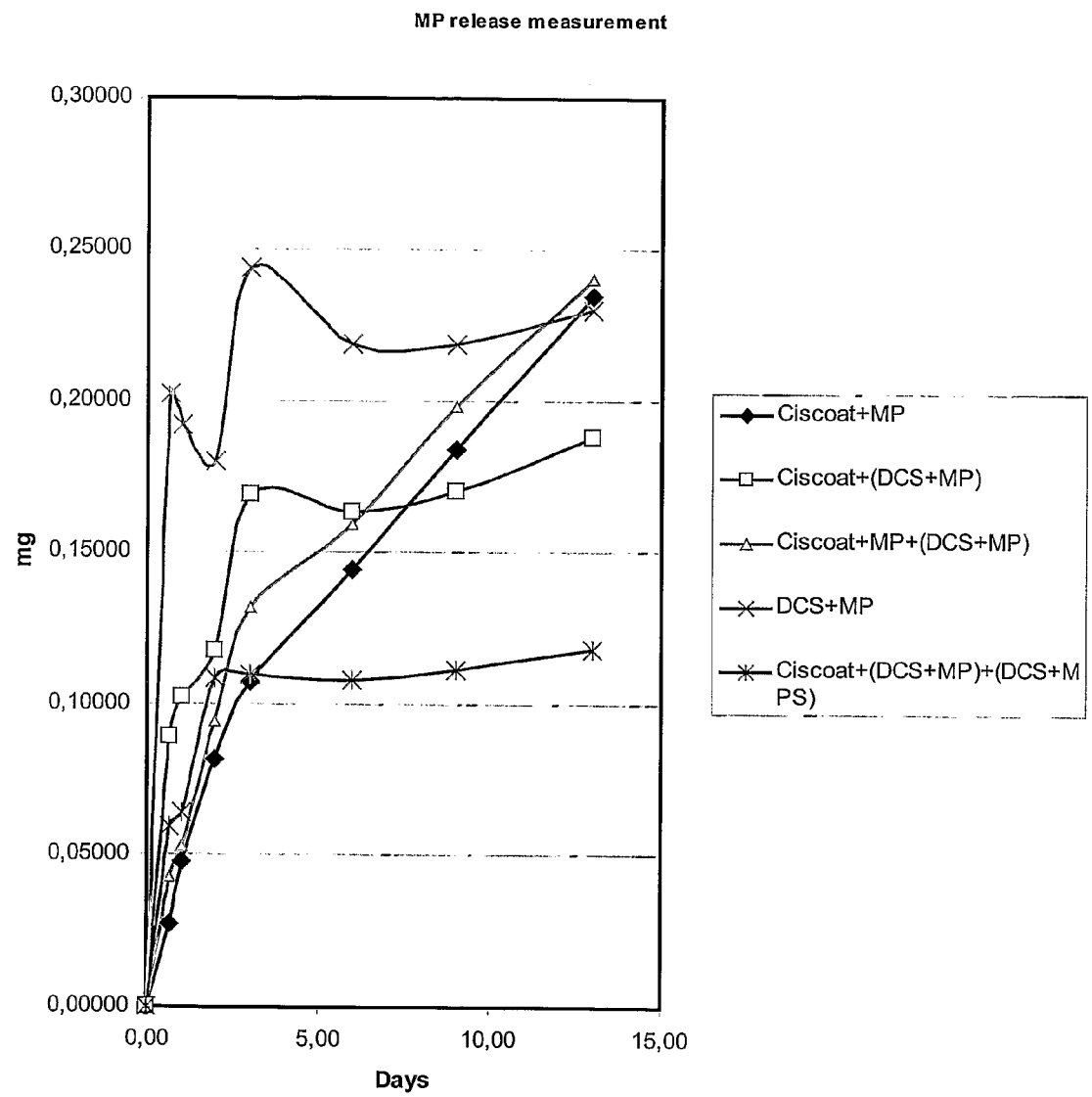
FIG. 11: Release curves of methylprednisolone (MPS) from the following samples: MPS directly embedded in a Ciscoat matrix; MPS embedded within a molecular sieve embedded in a Ciscoat matrix; MPS embedded both directly in the matrix and in the molecular sieve particles comprised therein.
Figure 12:
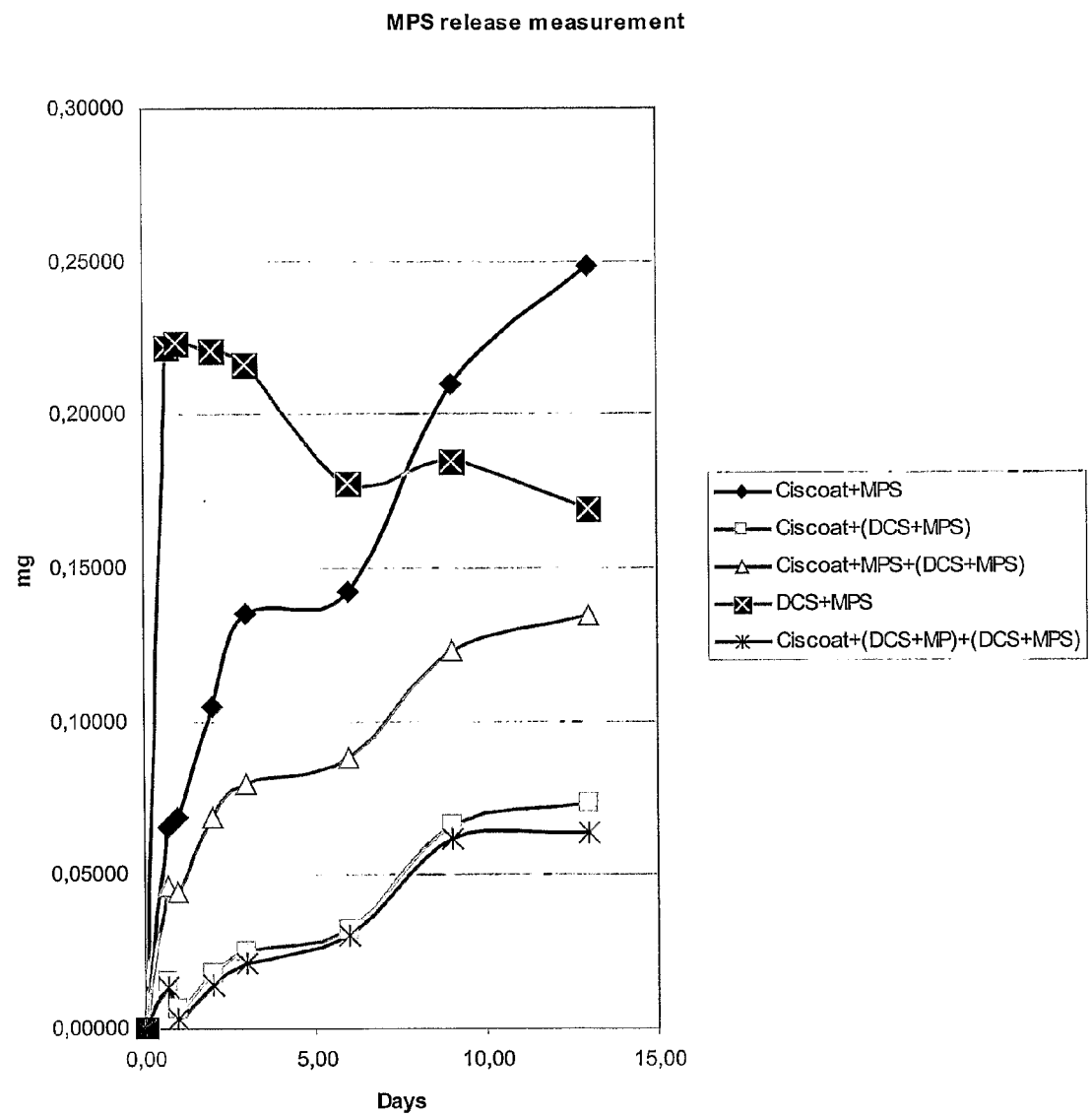
FIG. 12: Release curves of methylprednisolone (MP) from the following samples: MP directly embedded in a Ciscoat matrix; MP embedded within a molecular sieve (Drug-containing substrate or DCS) embedded in a Ciscoat matrix; MP embedded both directly in the matrix and in the molecular sieve particles comprised therein.

The drug release was measured by HPLC. The release curves are cumulative (decreases in the curves are due to the fact that for every measure a new calibration curve was used) The ordinate of the original curves was expressed in mg/ml. The used volume is 10 ml. The graph (FIGS. 11 and 12) display the total amount of drug released. Multiplication of the values by 10 provides the total amount of medicament that was released.

The invention claimed is:

1. An implantable medical device coated with a composition comprising:
   a) a coating matrix, and
   b) particles of one or more molecular sieves,
   wherein said coating matrix is a silicone matrix or a hydrophobic matrix,
   wherein said particles of said one or more molecular sieves comprise, within their pores, one or more bioactive agents,
   wherein the size of said pores of said one or more molecular sieve particles is selected to ensure controlled release rate of said bioactive agent,
   wherein said bioactive agent comprised within the pores of the molecular sieve is not an inorganic antimicrobial agent,
   wherein said implantable medical device comprises structural cavities on its inner and/or outer surface, and
   wherein the surface of said implantable medical device is not coated with said coating composition, with the exception of said structural cavities.

2. The implantable medical device of claim 1, wherein the surface of said implantable medical device is coated with a second matrix which is different from the matrix comprised in said structural cavities.

3. An implantable medical device coated with a composition comprising:
   a) a coating matrix, and
   b) particles of one or more molecular sieves,
   wherein said coating matrix is a silicone matrix or a hydrophobic matrix,
   wherein said particles of said one or more molecular sieves comprise, within their pores, one or more bioactive agents,
   wherein the size of said pores of said one or more molecular sieve particles is selected to ensure controlled release rate of said bioactive agent,
   wherein said particles of said one of more molecular sieves are embedded within said coating matrix,
   wherein said bioactive agent comprised within the pores of the molecular sieve is not an inorganic antimicrobial agent,
   wherein said implantable medical device comprises structural cavities on its inner and/or outer surface, and
   wherein the surface of said implantable medical device is not coated with said coating composition, with the exception of said structural cavities.

4. The implantable medical device of claim 3, wherein the surface of said implantable medical device is coated with a second matrix which is different from the matrix comprised in said structural cavities.

\* \* \* \* \*